(12) United States Patent
Guo et al.

(10) Patent No.: US 9,801,829 B2
(45) Date of Patent: Oct. 31, 2017

(54) METHODS AND SYSTEMS OF MAKING NANOSTRUCTURES

(75) Inventors: Peng Guo, Mountain View, CA (US); Charles R. Marin, Gainesville, FL (US); Yaping Zhao, Shanghai (CN); Richard N. Zare, Stanford, CA (US)

(73) Assignees: University of Florida Research Foundation, Inc., Gainesville, FL (US); The Board of Trustees of the Leland Stanford Junior University, Palo Alto, CA (US)

( * ) Notice: Subject to any disclaimer, the term of this patent is extended or adjusted under 35 U.S.C. 154(b) by 1364 days.

(21) Appl. No.: 13/457,609

(22) Filed: Apr. 27, 2012

(65) Prior Publication Data

US 2012/0294903 A1    Nov. 22, 2012

Related U.S. Application Data

(60) Provisional application No. 61/480,500, filed on Apr. 29, 2011.

(51) Int. Cl.
| | |
|---|---|
| *B82Y 40/00* | (2011.01) |
| *B82Y 5/00* | (2011.01) |
| *B01J 19/24* | (2006.01) |
| *A61K 9/51* | (2006.01) |
| *C08L 5/08* | (2006.01) |
| *A61K 47/36* | (2006.01) |
| *A61K 35/12* | (2015.01) |
| *A61K 9/00* | (2006.01) |
| *A61K 9/70* | (2006.01) |

(52) U.S. Cl.
CPC ......... *A61K 9/5161* (2013.01); *B01J 19/2475* (2013.01); *B82Y 5/00* (2013.01); *B82Y 40/00* (2013.01); *C08L 5/08* (2013.01); *A61K 9/70* (2013.01); *B01J 2219/00177* (2013.01)

(58) Field of Classification Search
CPC ..... A61K 9/5161; B01J 19/24; B01J 19/2475; B01J 2219/00164; B01J 2219/00177; B01J 2219/00186; C08L 5/08; B82Y 5/00; B82Y 40/00
See application file for complete search history.

(56) References Cited

U.S. PATENT DOCUMENTS

| | | | | |
|---|---|---|---|---|
| 5,565,215 | A | * | 10/1996 | Gref et al. ..................... 424/501 |
| 2009/0074824 | A1 | * | 3/2009 | Vila Pena ................ A61K 8/11 514/1.1 |

FOREIGN PATENT DOCUMENTS

FR    WO 2006067307 A1 *  6/2006  .............. B01J 13/14

OTHER PUBLICATIONS

Yu et al.; "Synthesis of carbon nanotubes within Pt nanoparticles-decorated AAO template," 2007, Elsevier; Materials Letters, vol. 61, pp. 97-100.*

(Continued)

*Primary Examiner* — Tigabu Kassa
*Assistant Examiner* — Ivan Greene
(74) *Attorney, Agent, or Firm* — Thomas|Horstemeyer, LLP

(57) ABSTRACT

In accordance with the purpose(s) of the present disclosure, as embodied and broadly described herein, embodiments of the present disclosure, in one aspect, relate to methods of making nanostructures (e.g., nanoparticles, nanofibers), systems for making nanostructures, and the like.

14 Claims, 12 Drawing Sheets

(56) References Cited

OTHER PUBLICATIONS

Martin et al.; "Tailored Polymer-Based Nanofibers and Nanotubes by Means of Different Infiltration Methods into Alumina Nanopores," 2009; ACS; Langmuir, vol. 25, No. 2, pp. 1181-1187.*

Guo et al.; "General Method for Producing Organic Nanoparticles Using Nanoporous membranes," 2010; ACS; Nano Letters vol. 10, pp. 2202-2206.*

Zhao et al.; "Nanoparticle synthesis in microreactors," 2010; Elsevier; Chemical Engineering Science, vol. 66, pp. 1463-1479.*

Guo et al.; "General Method for Producing Organic Nanoparticles Using Nanoporous Membranes," published online May 4, 2010; American Chemical Society, Nano Letters,vol. 10, pp. 2202-2206.*

Mao et al.; "General, Room-Temperature Method for the Synthesis of Isolated as Well as Arrays of Single-Crystalline ABO4-Type Nanorods," 2004; American Chemical Society, Journal of the American Chemical Society, vol. 126, pp. 15245-15252.*

Zhou et al.; "A Facile and Mild Synthesis of 1-D ZnO, CuO, and α-Fe2O3 Nanostructures and Nanostructured Arrays," 2008; American Chemical Society, ACSNano, vol. 2, No. 5, pp. 944-958.*

Guo et al.; "General Method for Producing Organic Nanoparticles Using Nanoporous Membranes," published online May 4, 2010; American Chemical Society, Nano Letters,Vol10, pp. 2202-2206.*

Mao et al.; "General, Room-Temperature Method for the Synthesis of Isolated as Well as Arrays of Single-Crystalline ABO4-Type Nanorods," 2004; American Chemical Society, Journal of the American Chemical Society, Vol126, pp. 15245-15252.*

Wong et al.; "Ambient Template-Directed Synthesis of Single-Crystalline Alkaline-Earth Metal Fluoride Nanowires," 2006; Wiley-VCH, Advanced Materials, vol. 18, pp. 1895-1899.*

Zhou et al.; "A Facile and Mild Synthesis of 1-D ZnO, CuO, and a-Fe2O3 Nanostructures and Nanostructured Arrays," 2008; American Chemical Society, ACSNano, vol. 2, No. 5, pp. 944-958.*

Charcosset et al.; "Preparation of nanoparticles with a membrane contactor," 2005, Elsevier; Journal of Membrane Science, vol. 266, pp. 115-120.*

Marinakos et al.; "Gold Nanoparticles as Templates for the Synthesis of Hollow Nanometer-Sized Conductive Polymer Capsules," 1999, Wiley-VCH; Advanced Materials, vol. 11, No. 1, pp. 34-37.*

Charcosset, Catherine; "Membrane processes in biotechnology: An overview," 2006, Elsevier; Biotechnology Advances, vol. 24, pp. 482-492.*

Chen et al.; "Amorphous Carbon Nanotubes with Tunable Properties via Template Wetting," 2006, Wiley-VCH; Advanced Functional Materials, vol. 16, pp. 1476-1480.*

ScienceDaily article "Microbes Convert Styrofoam Into Biodegradable Plastic," 2006; pp. 1-3.*

ScienceDaily article "Mity mealworms: Solution for food insecurity, pollution," 2016, pp. 1-3.*

Lewis, Richard J. editor.; Hawley's Condensed Chemical Dictionary, 2007. Wiley-Interscience; pp. 270 and 925.*

Kean, Thomas et al.; "Trimethylated chitosans as non-viral gene delivery vectors: Cytotoxicity and transfection efficiency," 2005, Elsevier; Journal of Controled Release, vol. 103, pp. 643-653.*

* cited by examiner

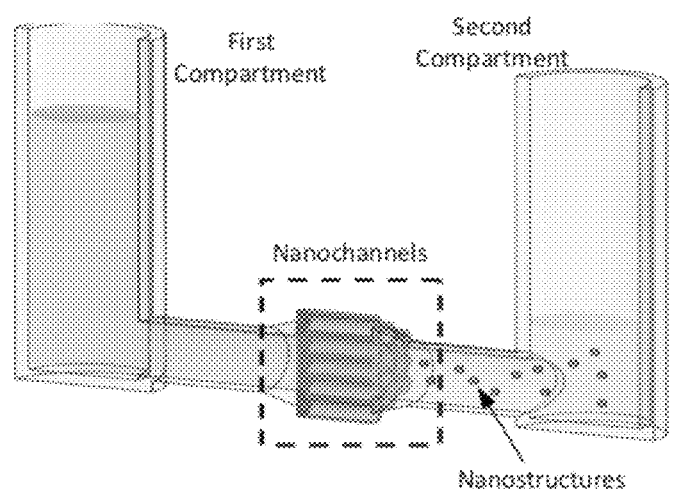
FIG. 1.1
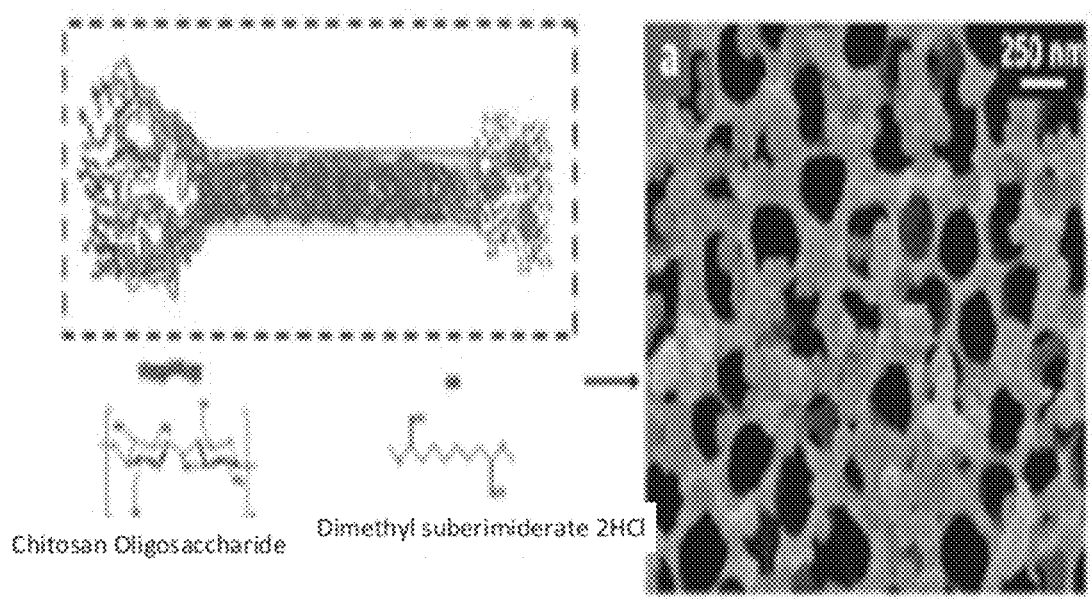
FIG. 1.2

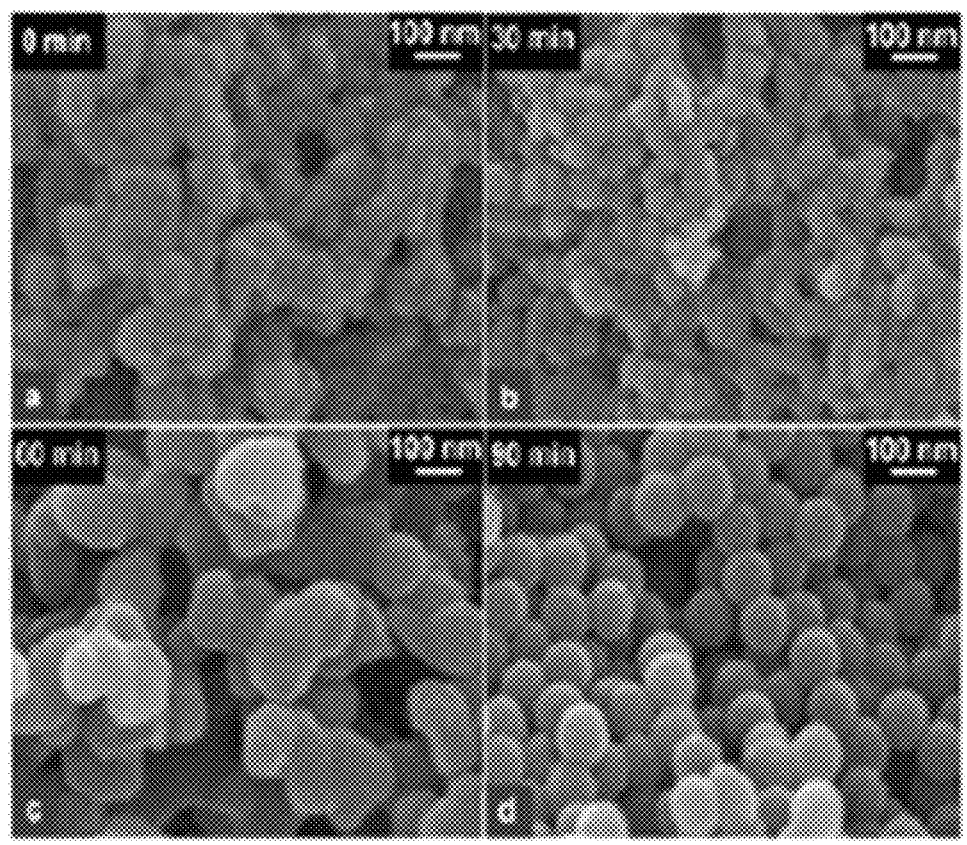
FIG. 1.3

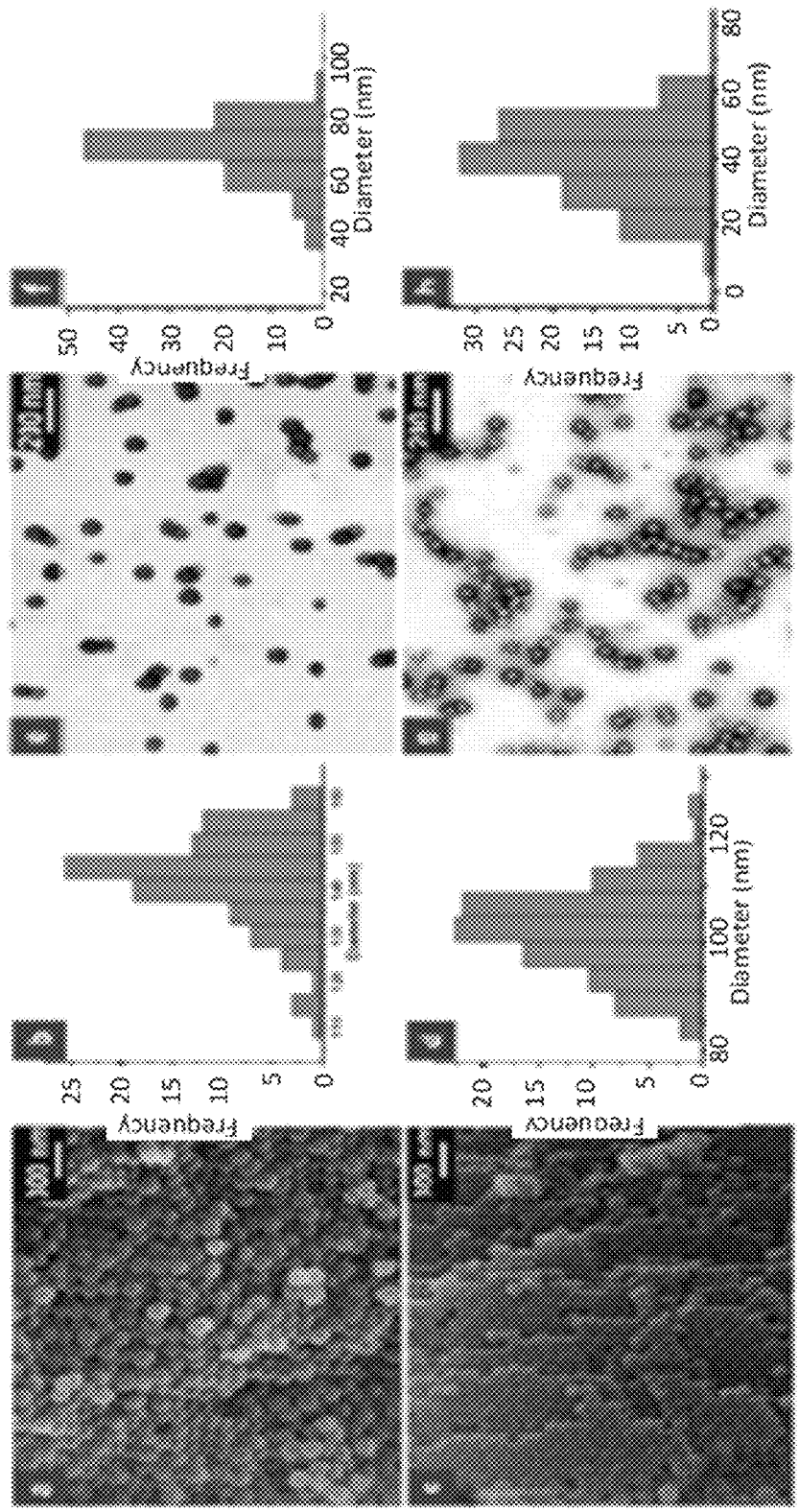
FIG. 1.4

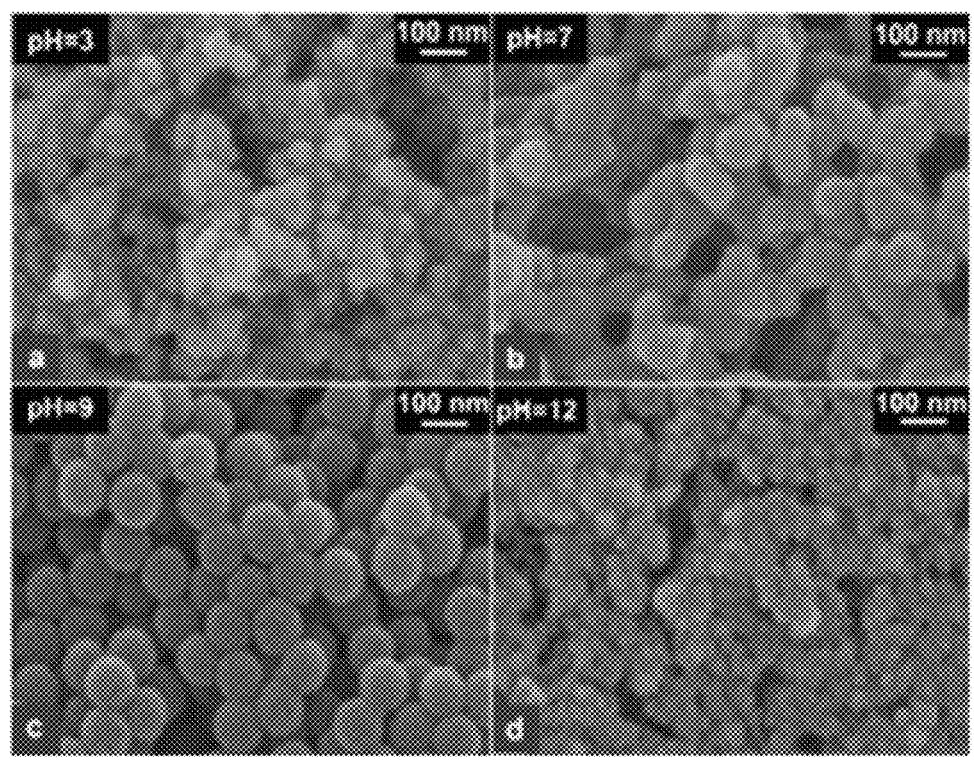
FIG. 1.5
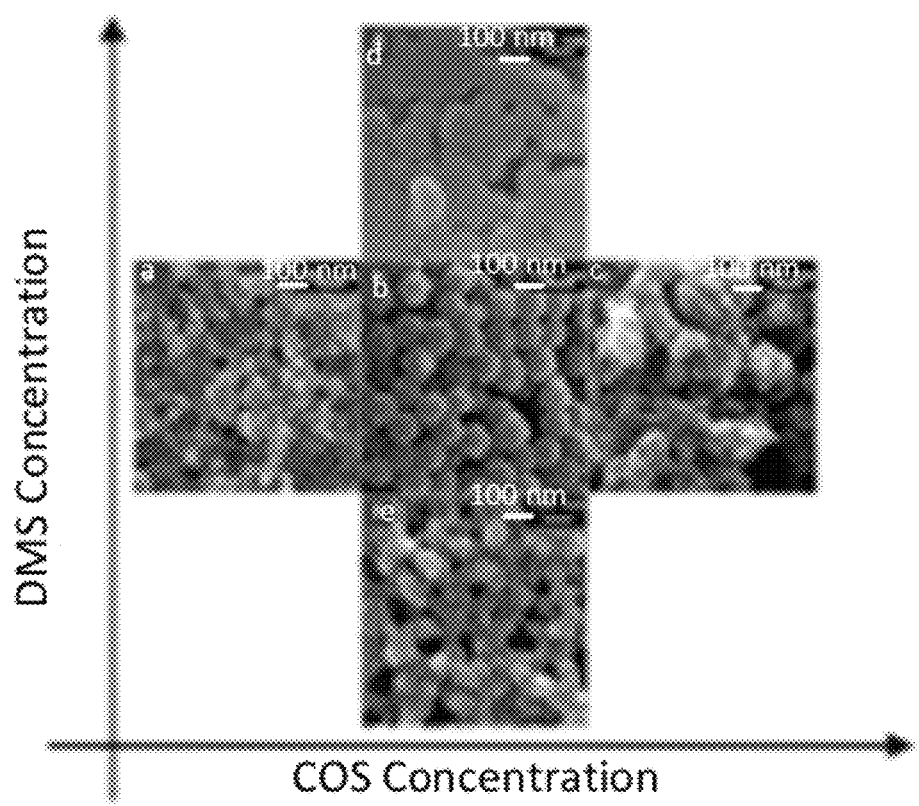
FIG. 1.6

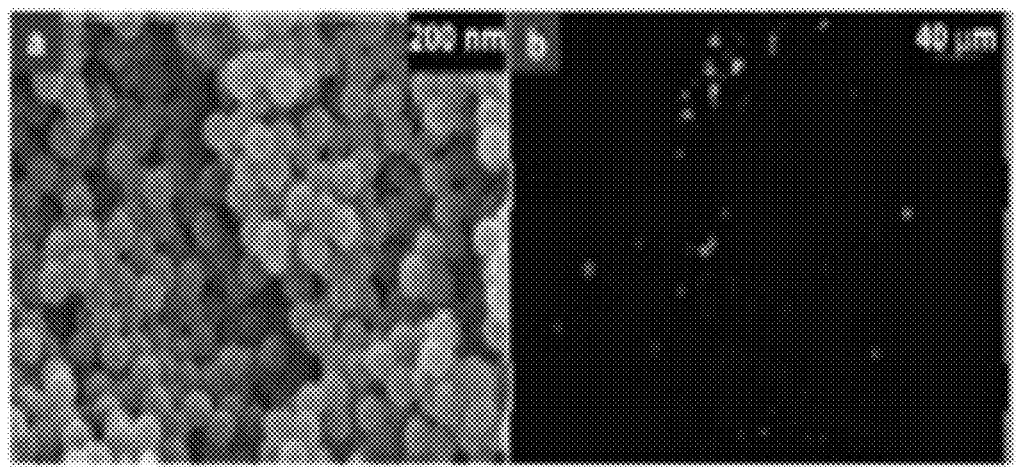
FIG. 1.7
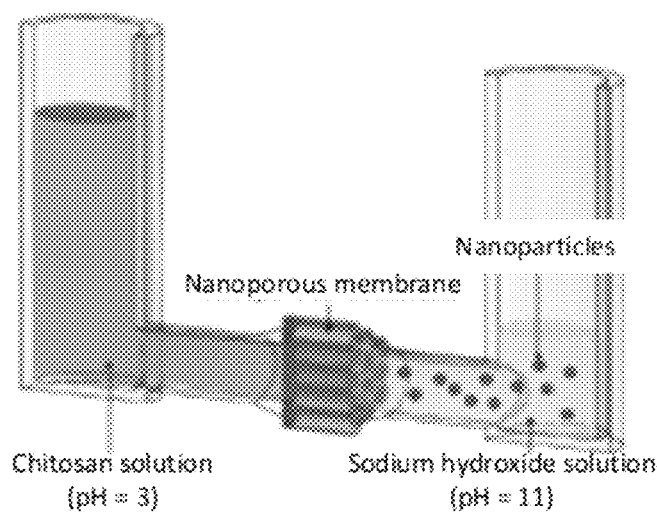
FIG. 2.1

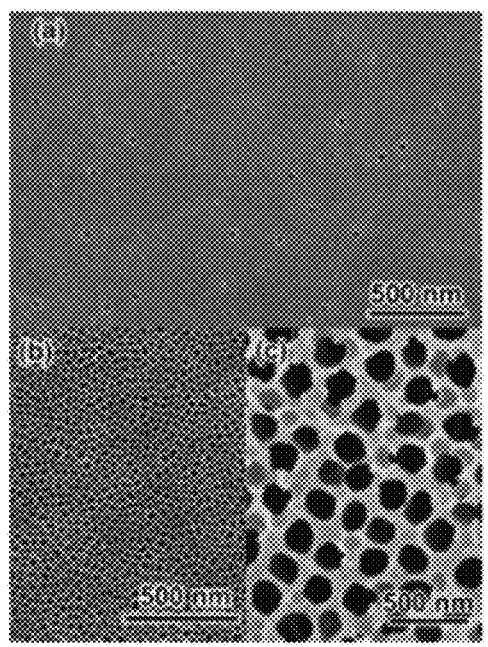
FIG. 2.2
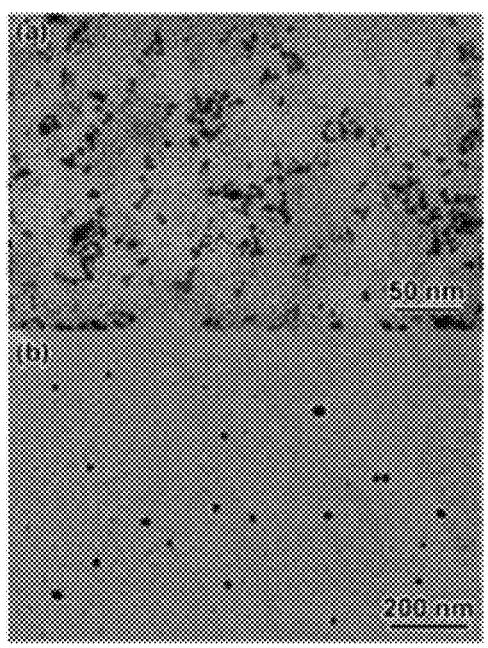
FIG. 2.3

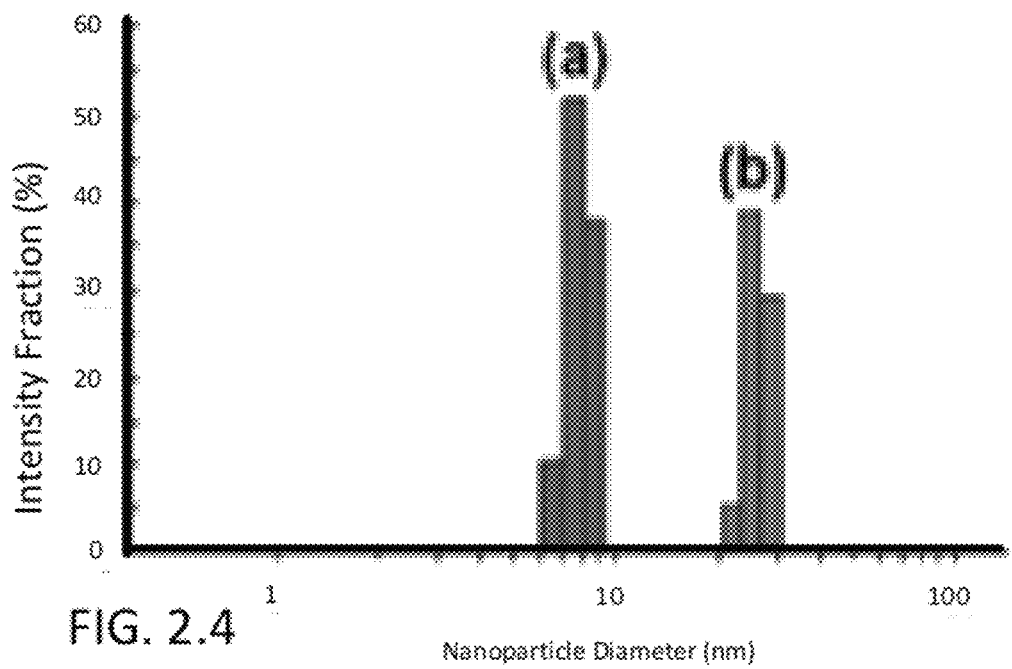
FIG. 2.4
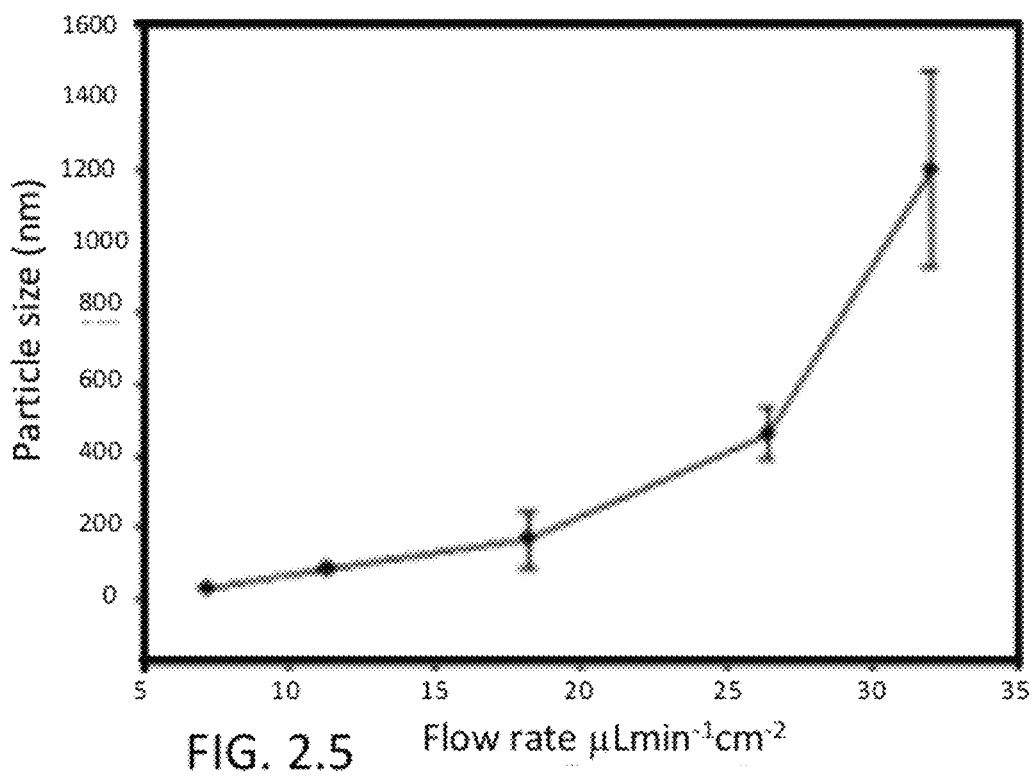
FIG. 2.5

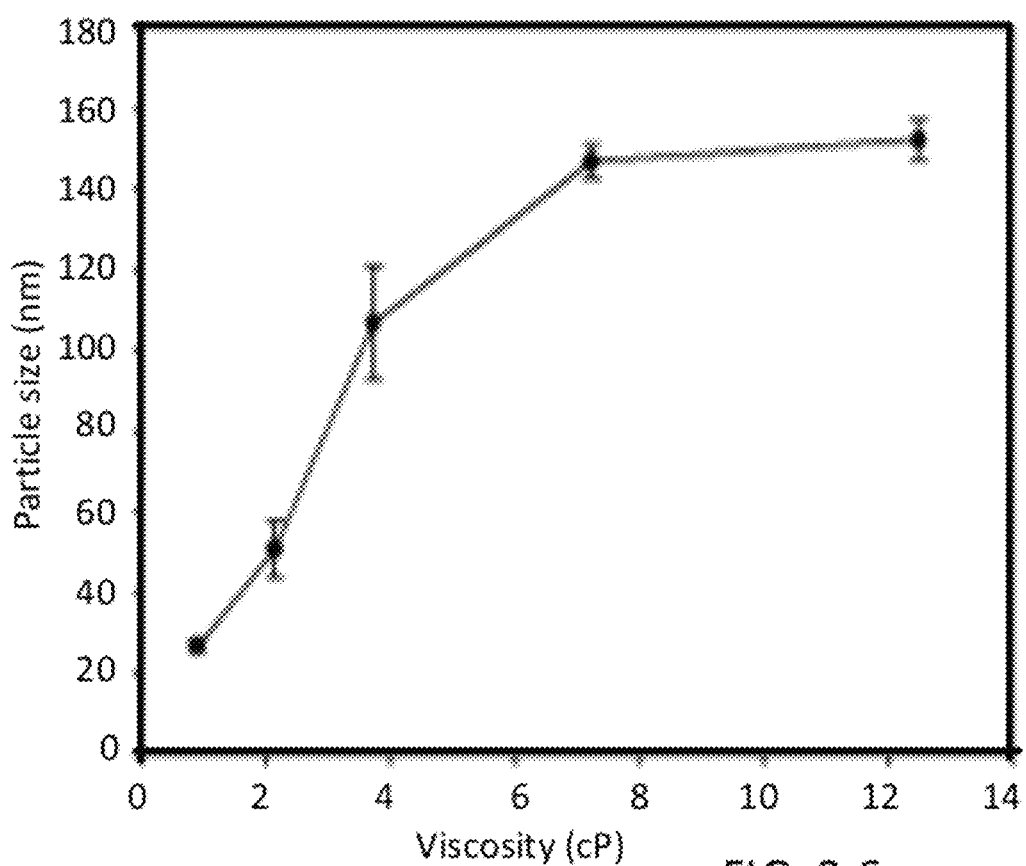
FIG. 2.6
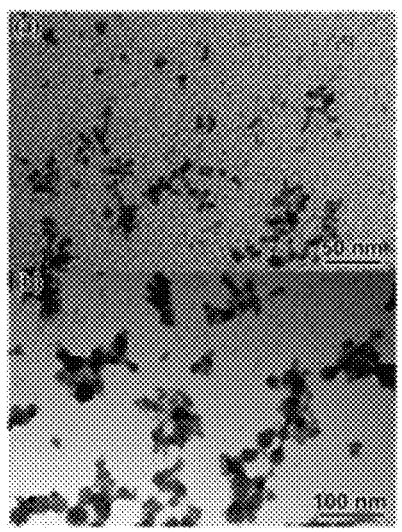
FIG. 2.7

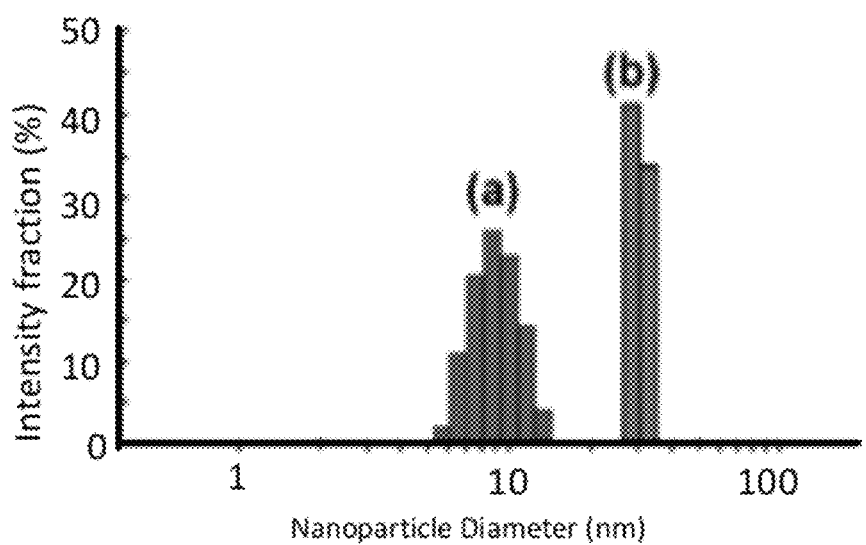
FIG. 2.8
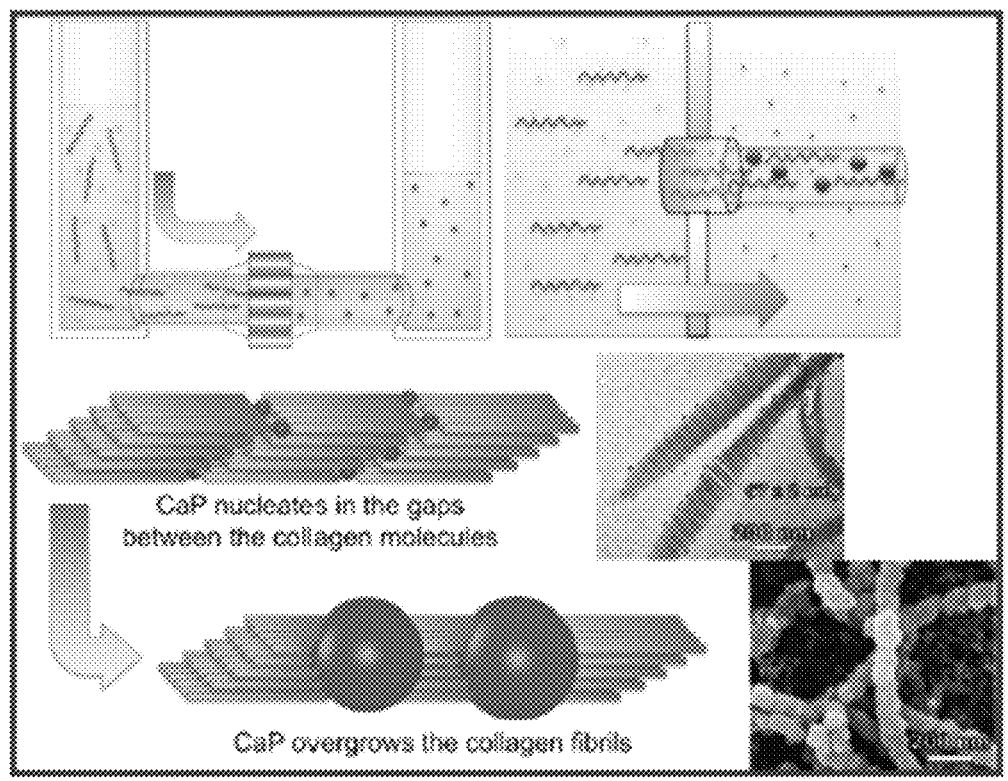
FIG. 3.1

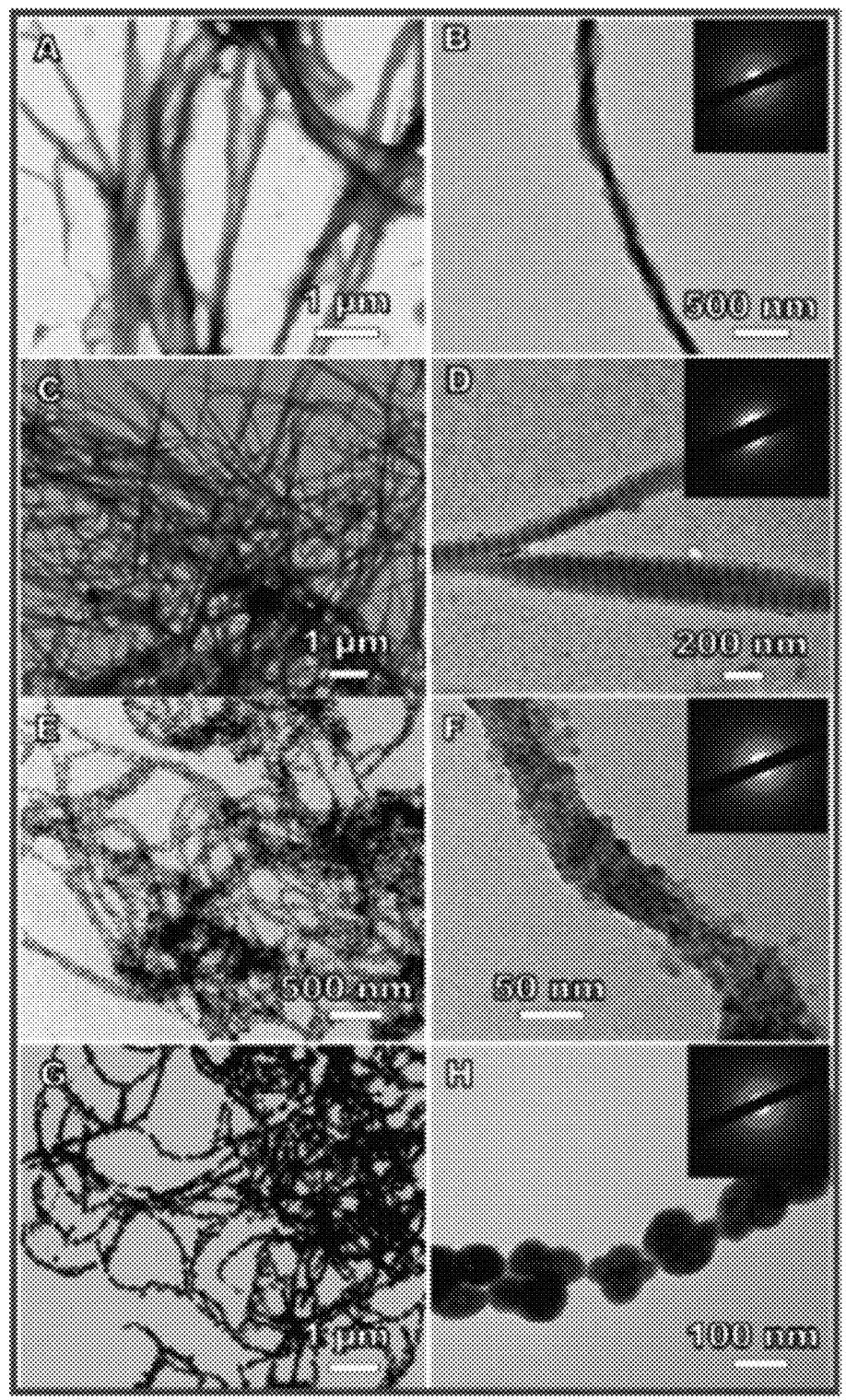
FIG. 3.2

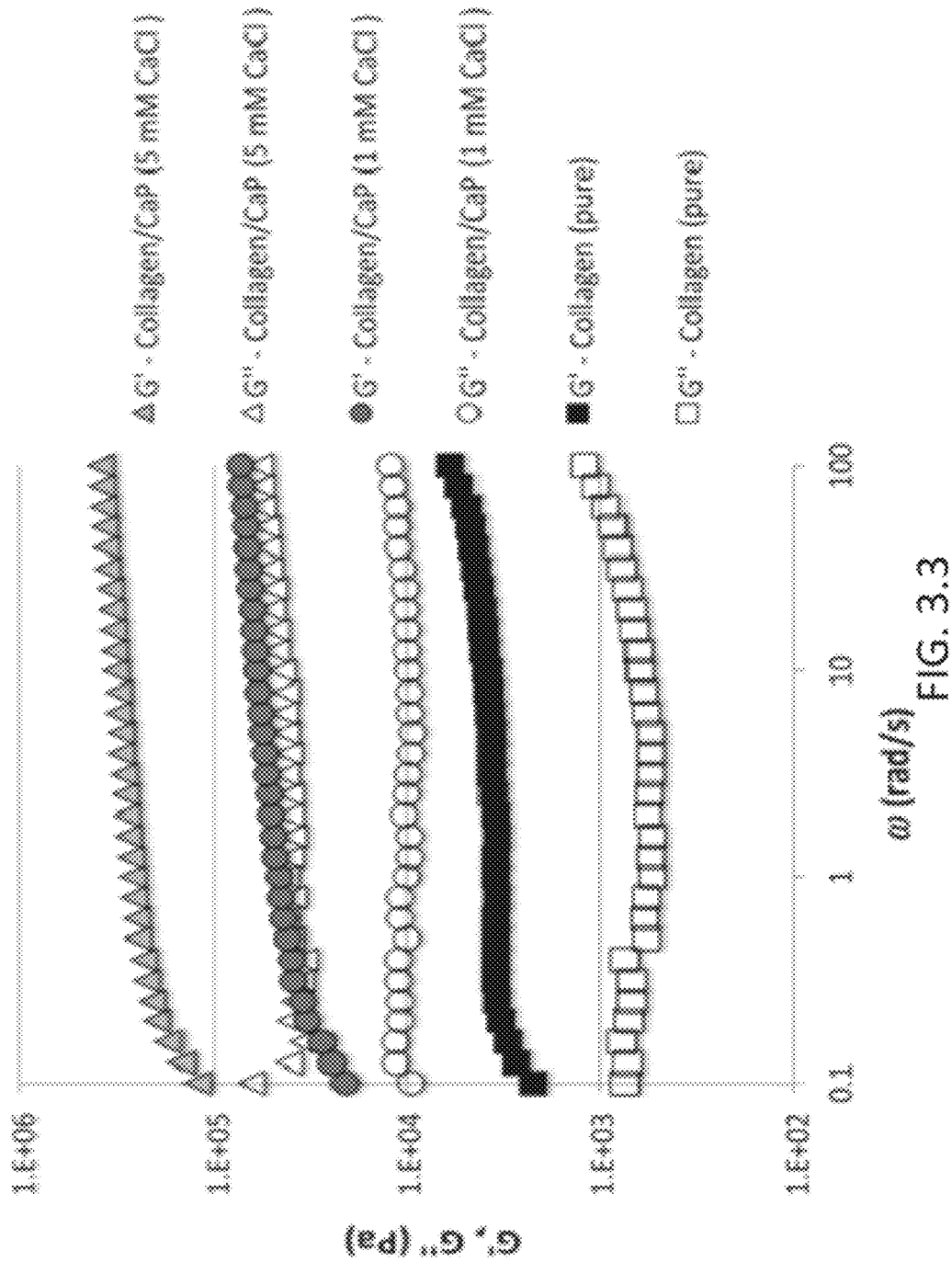
FIG. 3.3

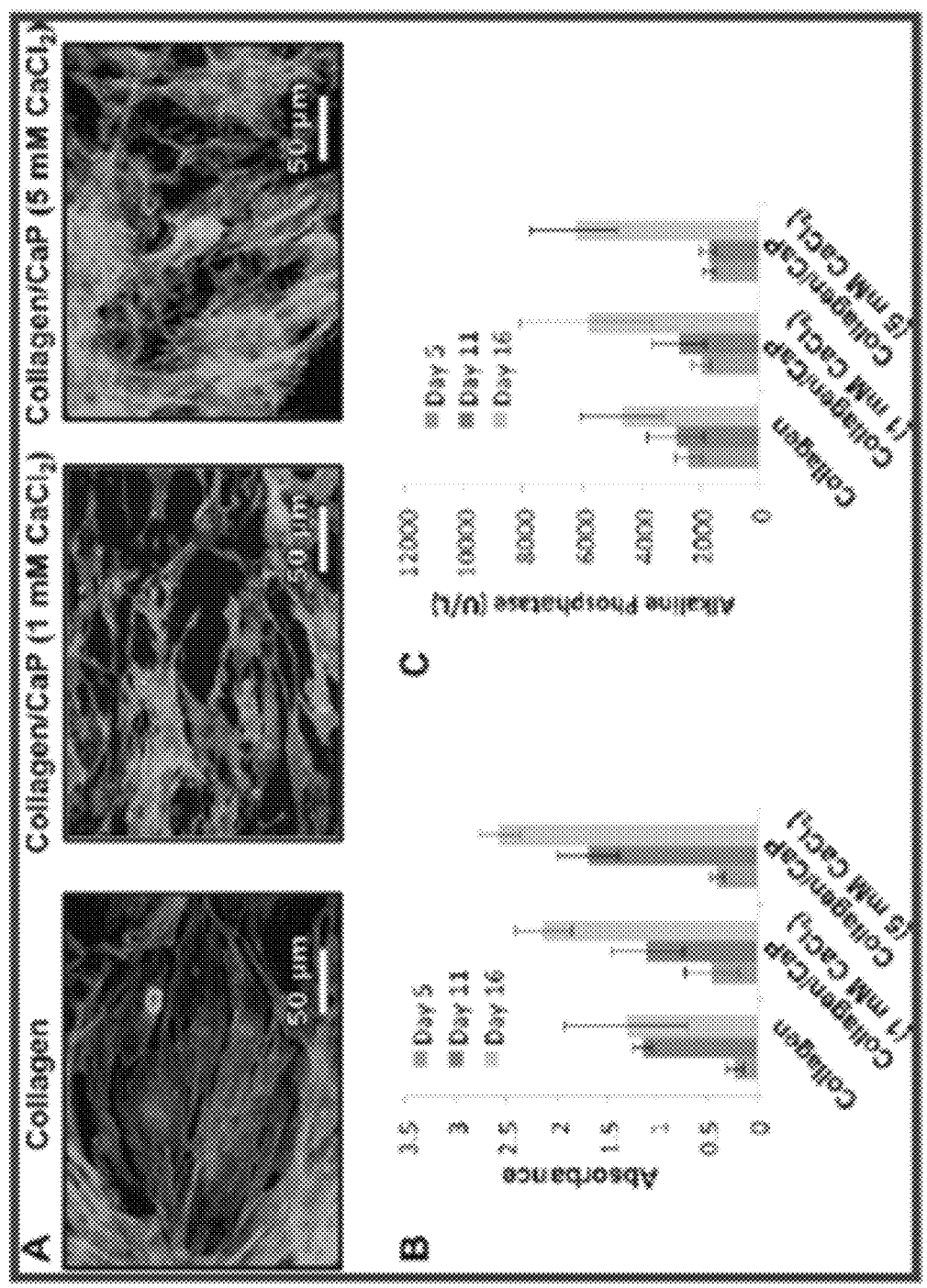
FIG. 3.4

METHODS AND SYSTEMS OF MAKING NANOSTRUCTURES

CROSS-REFERENCE TO RELATED APPLICATION

This application claims priority to U.S. provisional application entitled "METHODS OF MAKING NANOSTRUCTURES," having Ser. No. 61/480,500, filed on Apr. 29, 2011, which is entirely incorporated herein by reference.

STATEMENT REGARDING FEDERALLY SPONSORED RESEARCH OR DEVELOPMENT

This invention was made with Government support under contract CA125467 awarded by the National Institutes of Health. The Government has certain rights in this invention.

BACKGROUND

Making particles, such as nanoparticles, in a simple and inexpensive manner has received significant interest. Of particular interest are delivery systems, such as drug delivery systems, that can be tailored for controlled release. In addition, methods of making nanofibers are important in the area of tissue engineering. However, present techniques have for making nanoparticles and nanofibers provide a number of challenges. Thus, there is a need to address and overcome at least some of these challenges.

SUMMARY

Embodiments of the present disclosure provide for methods of making nanostructures (e.g., nanoparticles, nanofibers), systems for making nanostructures, and the like.

An embodiment of the present disclosure includes a method of making nanostructures, among others, including providing a structure having a first compartment for a first fluid and a second compartment for a second fluid, wherein a membrane structure having nanochannels is positioned between the first compartment and second compartment; causing the first fluid to flow through the membrane structure from the first compartment to the second compartment; and forming nanostructures. In an embodiment, forming includes forming nanostructures at the opening of the nanochannel.

An embodiment of the present disclosure includes a system for making nanostructures, among others, including a structure having a first compartment for a first fluid and a second compartment for a second fluid, wherein the structure has nanochannels positioned between the first compartment and second compartment, wherein the first fluid is caused to flow through the structure from the first compartment to the second compartment to form nanostructures.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates two separate solutions are in contact through a membrane having well-defined nanopores.

FIG. 1.2 is a schematic representation of the preparation of chitosan nanoparticles with branched alumina nanoporous membrane.

FIG. 1.3 illustrates intermediate chitosan nanoparticles during polymerization at various ultrasonication time: (a) 0 min; (b) 30 min; (c) 60 min and (d) 90 min.

FIG. 1.4 illustrates the distribution of 100 random nanoparticles prepared under various temperature (b, d, f and h) and typical SEM (a, c), TEM (e, g) images: (a) 10° C.; (c) 25° C.; (e) 40° C.; (g) 60° C.

FIG. 1.5 illustrates intermediate chitosan nanoparticles during polymerization at various pH value: (a) pH=3; (b) pH=7; (c) pH=9 and (d) pH=12. The rate of amidine cross-linking between COS and DMS is pH dependent, which reaches a pH-rate maxima at pH=9. Higher or lower pH value results in insufficient cross-linking.

FIG. 1.6 illustrates intermediate chitosan nanoparticles during polymerization at various COS and DMS concentration.

FIG. 1.7 illustrates FITC-labeled chitosan nanoparticles (a) Typical SEM image; (b) Fluorescence micrograph.

FIG. 2.1 illustrates a method for producing chitosan nanoparticles by flow though a nanoporous membrane.

FIG. 2.2 illustrates SEM images of nanoporous membranes. (a) Track-etched polycarbonate (PCTE) membrane with 10 nm pores; AAO membrane with (b) a 20 nm inlet and (c) a 200 nm outlet.

FIG. 2.3 illustrates typical TEM images of chitosan nanoparticles (CSNPs) prepared by using (a) the PCTE membrane and (b) the AAO membrane. In these TEM images, the black area represents the nanoparticle, and the gray area represents the background.

FIG. 2.4 illustrates a comparison of size distributions of chitosan nanoparticles (CSNPs) prepared by using different nanoporous membranes determined by dynamic light scattering (a) size of CSNPs obtained by PCTE membrane and (b) size of CSNPs obtained by AAO membrane.

FIG. 2.5 illustrates the effect of solution flow rate on the diameter of the chitosan nanoparticle.

FIG. 2.6 illustrates the effect of the viscosity of the chitosan feed solution on the diameter of the nanoparticles obtained.

FIG. 2.7 illustrates typical TEM images of chitosan-rhodamine 6G nanoparticles prepared by using (a) the PCTE membrane and (b) the AAO membrane. In these TEM images, the black area represents the nanoparticle, and the gray area represents the background.

FIG. 2.8 illustrates a comparison of size distributions of chitosan-rhodamine 6G nanoparticles prepared by using different nanoporous membranes determined by dynamic light scattering. (a) PCTE membrane and (b) AAO membrane.

FIG. 3.1 illustrates experimental setup and proposed model for the formation of mineralized collagen fibrils. Amorphous calcium phosphate formed inside or near the exit of the nanopores simultaneously with the self-assembly of collagen fibrils. The fibrils were extruded from the pores in the direction of the feed solution flow. The upper inset is a transmission electron micrograph of the mineralized collagen fibrils showing visual enhancement of the periodic banding structure as a result of the incorporation of CaP. The lower inset is a scanning electron micrograph of the collagen fibrils showing the overgrowth of CaP.

FIG. 3.2 illustrates collagen fibrils: (A, B) unmineralized; (C, D) mineralized (1 mM $CaCl_2$ in feed solution); (E, F) mineralized (2.5 mM $CaCl_2$); and (G, H) mineralized (5 mM $CaCl_2$). The fibrils were produced using a pore diameter of 200 nm. The insets in (B, D, F, H) are selected area electron diffraction images showing that the mineral portion is amorphous.

FIG. 3.3 illustrates rheological measurements of gels derived from different types of collagen fibrils.

FIG. 3.4 illustrates: (A) Fluorescent microscopy images of hADSCs cultured on different fibrils in which green indicates actin filaments and blue indicates cell nuclei. (B) Results as a function of time of the CellTiter 96 assay indicating proliferation of hADSCs on collagen fibrils. (C) Alkaline phosphatase production from hADSCs cultured on collagen fibrils as a function of time. The $CaCl_2$ concentrations refer to the concentrations in the feed solution.

DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, nanotechnology, biochemistry, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Discussion

In accordance with the purpose(s) of the present disclosure, as embodied and broadly described herein, embodiments of the present disclosure, in one aspect, relate to methods of making nanostructures (e.g., nanoparticles, nanofibers), systems for making nanostructures, and the like. An embodiment of the present disclosure is advantageous in that the morphology (e.g., size and shape) of the nanostructures can be controlled using a continuous flow system where two fluids are mixed using a structure including nanochannels (e.g., membrane structure), where the structure is positioned between the two fluids. In an embodiment, the morphology of the nanostructures can be controlled by adjusting one or more other parameters (e.g., components, length and size of nanochannels, sonication, temperature, pH, reactant concentration, pressure). In addition, two or more types of materials in one of the fluids can be combined to form the nanostructures, which can be advantageous if one of the materials is not very soluble in water and the other material is soluble in water. In addition, the nanostructures can include another component such as drug molecules, calcium phosphate, gene materials, and the like, that can be incorporated into the nano structures.

In an embodiment, the system (See FIG. 1.1) for forming the nanostructures includes a structure having a first compartment for a first fluid and a second compartment for a second fluid. In an embodiment, the structure includes nanochannels positioned between the first compartment and second compartment. In an embodiment, the nanochannels can be a separate membrane structure that can be inserted and removed from between the first compartment and the second compartment, where the nanochannels form a membrane. In an embodiment, the first fluid is caused to flow through the nanochannels from the first compartment to the second compartment to form nanostructures upon mixing with the second fluid and/or a change in a condition (e.g., solvent, pH, temperature, salt content, solubility, chemical concentration). Additional details regarding the system and methods are provided herein and in the Examples.

As mentioned above, methods of the present disclosure can be used to make nanostructures. The nanostructure that can be formed can include a nanoparticle, a nanowire, a nanofiber, a nanotube (a hollow nanowire), a nanosheet, and a combination of these. One or more dimensions of the nanostructure (e.g., width and height, or diameter, and length) can be controlled by the dimensions (e.g., diameter and length) of the nanochannel. In an embodiment, chitosan nanoparticles and collagen fibers can be produced as described in more detail in the Examples.

In general, one or more of the dimensions of the nanostructure is about 1 to 1 μm or about 1 to 500 nm. In a particular embodiment, a nanoparticle can have a diameter of about 1 nm to 1 μm, about 1 nm to 500 nm, about 5 to 100 nm, or about 5 to 30 nm. In a particular embodiment, a nanowire, nanofiber, or nanotube can have a diameter of about 1 nm to 1 μm or about 1 nm to 500 nm, and a length of about 1 nm to 100 μm or more or about 1 nm to 10 μm. In a particular embodiment, a nanosheet can have a width of about 1 nm to 1 μm or about 1 nm to 500 nm, and a length of about 1 nm to 100 μm or more or about 1 nm to 10 μm.

In an embodiment, the method includes making nanostructures by causing two fluids to mix with one another. In an embodiment, a first fluid is disposed in a first compartment (e.g., can be made of plastic, metal, and the like, and can hold a volume of a few milliliters to 10's of liters), while a second fluid is disposed in a second compartment (e.g., can be made of plastic, metal, and the like, and can hold a volume of a few milliliters to 10's of liters). A structure (e.g., a structure membrane) including one or more nanochannels is positioned between the first compartment and the second compartment, where the first fluid and/or the second fluid can flow through the nanochannels and into the other compartment. The dimensions (e.g., length, width, and/or height) of the structure including the nanochannels can vary from nanometers to meters. The fluids can mix in and/or at the opening of a nanochannel. In an embodiment, the nanoparticles are formed at the opening of the nanochannels. In an embodiment, the structure can be a membrane and include a plurality of nanopores. In an embodiment, the structure including the nanochannels can be made of a material such as a polymer (e.g., polycarbonate), an inorganic material (e.g., aluminum oxide), and a combination thereof, where the material is able to operate (e.g., structurally, chemically) under the conditions placed upon the structure (e.g., pressure, temperature, pH, salt content). In an embodiment, the nanochannels of the structure are made of a material such as anodized aluminum oxide, polycarbonate, polyethylene terephthalate, kapton, mica, glass, silicon, graphene, and the like. In an embodiment, the nanochannels of the structure can be an anodized aluminum oxide membrane or a polycarbonate track etched (PCTE) membrane.

In an embodiment, the structure includes about 1 to $10^{15}$ nanochannels per μm². In an embodiment, the structure includes about 1 to $10^{15}$ nanochannels or more. In an embodiment, the nanochannel can have a diameter of about 1 nm to 1 μm or about 1 nm to 500 nm. In an embodiment, the nanochannel can have a length of about 1 nm to 100 μm or more or about 1 nm to 500 μm. In an embodiment, the diameter of the nanochannel along the length can be tapered from narrower to wider (e.g., the narrower portion can be facing either the first or the second compartment). If the nanochannel does not have a circular cross-section or substantially circular cross-section, then the width and height can each independently be about 1 nm to 1 μm or about 1 nm to 500 nm. In an embodiment, the nanochannels are made of anodized aluminum oxide that have nanochannels having a diameter of about 1 to 500 nm and a length of about 1 nm to 100 μm or more or about 1 nm to 500 μm. In an embodiment, the nanochannels made of the anodized aluminum oxide can have a diameter of about 20 nm that tapers to 200 nm at the end of the nanochannel. In an embodiment, the shape of nanochannel cross-section can be polygonal. In an embodiment, the shape of nanochannel cross-section could be variable, from circular to triangular, or quadrangular.

As mentioned above, the fluids are mixed in or at the exit of a nanochannel. In an embodiment the fluids are caused to mix as a result of a flow caused by an osmotic flow, a pressure flow, an electrophoretic flow, gravity flow, or a combination thereof. One or more of these flows can be used to mix the fluids in a continuous manner.

In an embodiment, the method includes making nanostructures by causing two fluids to mix with one another under a certain condition(s) in and/or at the exit of a nanochannel. The first fluid and/or the second fluid can be selected so that each are under certain conditions, and when the fluids mix, the condition(s) of the mixture is altered relative to that of the first and the second fluid. In an embodiment, the change in the condition(s) can cause the nanostructure to form (e.g., precipitation). In an embodiment, the condition can include pH, temperature, salt content, solubility, chemical concentration, or a combination thereof.

One or both of the first fluid and the second fluid can include one or more chemicals that can be used to form the nanostructure. In an embodiment, the chemical(s) can be dissolved in or be the fluid under certain conditions, but form the nanostructure once the conditions are changed. In an embodiment, the concentration of the dissolved chemical can be varied to produce to the desired nanostructure. In an embodiment, the chemical may not be dissolved or only partially dissolved in the fluid. The types of fluids and/or chemical(s) selected depend, at least in part, upon the desired nanostructure to be formed. In addition, the pH, temperature, salt content, and/or concentration of the chemical can be varied depending upon the desired nanostructure to be formed. For example, as the temperature is increased, the nanoparticle size may decrease. In another example, nanoparticles are only formed after the fluid(s) are sonicated (e.g., ultrasonication).

In an embodiment, one or both of the fluids can include one or more of a monomer (e.g., monomolecular tropocollagen), oligomer (e.g., chitosan), a polymer, an ion, crosslinkers, small organic molecules (e.g., a drug), gene materials (e.g. DNA or RNA), and combinations thereof. In an embodiment, one or both of the fluids can include one or more biodegradable chemicals, pharmaceutical agents, nucleic acids, proteins, and combinations thereof. In an embodiment, one or both fluids can include ions, an organic molecule, a lipid, a pharmaceutical agent, a protein, a gene material, a molecular imaging probe (e.g., fluorescence dyes, near infrared dyes, radioactive molecules, isotypes, magnetic resonance imaging (MRI) agents), or a combination thereof. Exemplar fluids, conditions, flows, and nanostructures are described in the Examples.

In an embodiment, a sonic or ultrasonic energy can be applied to the structure including the nanochannels or the area adjacent the opening(s) of the nanochannels to affect the formation and/or morphology of the nanostructures. In another embodiment, mechanical force can be used to affect the formation and/or morphology of the nanostructures. In another embodiment, heat can be used to affect the formation and/or morphology of the nanostructures. In another embodiment, sonic or ultrasonic energy, mechanical force, and/or heat can be used to affect the formation and/or morphology of the nanostructures.

In an embodiment, the first fluid can be under a pressure flow and have an acidic pH and the second fluid can be under an osmotic flow and have a basic pH. The first fluid is a liquid form of the chemical that is to be formed into nanostructure. Once the first and second fluid mix, the pH changes to be close to neutral; and nanostructures are formed in or at the opening of the nanochannel. Thus, the flow of each of the fluids, the pH, and the chemical forming the first fluid in conjunction with the nanochannels can be used to produce nanostructures. Modification of any of these parameters or other parameters may be used to alter the morphology of the nanostructures. Additional details regarding embodiments of the present disclosure are provided in the Examples.

EXAMPLES

Now having described the embodiments of the present disclosure, in general, the examples describe some additional embodiments of the present disclosure. While embodiments of the present disclosure are described in connection with examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

FIG. 1.1 illustrates two separate solutions are in contact through a membrane having well-defined nanopores. One solution is made to flow into the other, causing molecules in the first solution to come together to form nanoparticles inside the nanopores of the membrane, which sets a limit on the size. Various parameters can be changed to alter the morphology of the nanoparticles. For example, the use of ultrasonication causes the formation of nanowires and nanosheets. The nanoparticles are found from scanning electron microscopy (SEM) images to be relatively uniform. Moreover, we have observed nanoparticles of polymer to be as small as approximately 10 nm.

FIG. 1.2 is a schematic representation of the preparation of chitosan nanoparticles with branched alumina membrane. Chitosan oligosaccharide (COS) and dimethyl suberimidate 2 HCl (DMS) solution are added separately on both side of AAO film. Ultrasonication is applied to break up aggregates and accelerate polymerization.

FIG. 1.3 illustrates intermediate chitosan nanoparticles during polymerization at various ultrasonication time: (a) 0 min; (b) 30 min; (c) 60 min and (d) 90 min.

FIG. 1.4 illustrates the distribution of 100 random nanoparticles prepared under various temperature (b, d, f and h) and typical SEM (a, c), TEM (e, g) images: (a) 10° C.; (c) 25° C.; (e) 40° C.; (g) 60° C. According to the Eotvos empirical equation, the surface tension decreases with increasing temperature generally. When surface tension is low, smaller nanoparticles are formed at anodized aluminum oxide (AAO) nanopore surface.

FIG. 1.5 illustrates intermediate chitosan nanoparticles during polymerization at various pH value: (a) pH=3; (b) pH=7; (c) pH=9 and (d) pH=12. The rate of amidine cross-linking between COS and DMS is pH dependent, which reaches a pH-rate maxima at pH=9. Higher or lower pH value results in insufficient cross-linking.

FIG. 1.6 illustrates intermediate chitosan nanoparticles during polymerization at various COS and DMS concentration.

FIG. 1.7 illustrates FITC-labeled chitosan nanoparticles (a) Typical SEM image; (b) Fluorescence micrograph.

Example 2

Brief Introduction

Two liquids are separated by a nanoporous membrane and one liquid is made to flow into the other, causing nanoparticles to be formed at the exits of the nanopores. In particular, we report the generation of nanoparticles of the biodegradable polysaccharide polymer chitosan by placing the chitosan in a low pH aqueous solution that is flowed into a high pH aqueous solution. The size of the nanoparticles (5-20 nm) can be roughly controlled by choosing the size of the nanopores and the pumping rate. In addition, it is possible to load the chitosan nanoparticles with drug molecules, which is demonstrated by incorporation of up to 3.3% rhodamine 6G molecules in the chitosan nanoparticles.
Introduction:

The spatial and temporal control of the release of pharmaceuticals at the site of where they act is a key requirement for the therapeutic use of a drug.[1-3] One method for realizing this objective is to create drug-loaded nanoparticles made out of biodegradable polymers.[4] Previous work in two laboratories, one at Stanford University, the other at the University of Florida, has featured the generation of such nanoparticles.[5-8] We present here an alternative strategy based on the use of a nanoporous membrane that separates the two liquids. By pumping one liquid into the other, through the membrane, we can generate nanoparticles at the exits of the membrane nanopores. We illustrate this technique for the low molecular weight biopolymer chitosan, which is a polysaccharide consisting of 13-17% units of monomeric N-acetyl-glucosamine and 83-87% glucosamine units:

Low molecular weight chitosan (average MW 20,000 Da) is used as a model polymer in our work because it is a naturally biodegradable and biocompatible polysaccharide, which has broad applications in pharmaceutical and biomedical fields.[10-12] Chitosan is also known as a pH-response polymer, because at low pH, chitosan's amines are protonated and positively charged causing chitosan to be a water soluble cationic polyelectrolyte. At high pH, these amines become deprotonated, and the polymer loses its charge and becomes insoluble.[13,14] Chitosan serves as a representative material for our process that can be adopted for the productions of other organic nanoparticles. In the case of chitosan, we use the precipitation caused by pH change, but other precipitation methods are applicable, such as temperature or antisolvent, or chemical reaction.

Droplet formation in liquid-liquid systems on the micrometer scale has been studied previously by Anna, Bontoux, and Stone.[15] Xu et al.[16] reported generating particles from microfluidic structures with sizes from 20 to 1000 μm. The closest paper involving particle generation on the nanoscale using nanopores appears to be the work of Powell et al.[17] who observed the transient formation and dissolution of nanoparticles in conical nanopores caused by the presence of permanent surface charges on the walls, whose electric field induces precipitation. The present work differs in that the nanoparticles are not formed inside the nanopores.

Procedure:

The experimental device (FIG. 2.1) is composed of a nanoporous membrane, which separates two solutions. The pH of the feed solution (left in FIG. 2.1) is adjusted so that chitosan is soluble in this solution. The feed solution is forced under pressure through the pores of the membrane into the receiver solution (right in FIG. 2.1). The pH of the receiver solution is adjusted such that chitosan is insoluble. When nanodroplets of the soluble chiotsan are injected through the membrane into the receiver solution nanoparticles of chitosan are formed at the exits of the nanopores.

For the preparation of nanoparticles with reduced sizes, membranes with uniform and well-defined nanopores are essential.[18-20] In our work, we use commercially available track-etched polycarbonate (PCTE, OSMONIC Inc.) and anodized aluminum oxide (AAO, Whatman Inc.) nanoporous membranes. The PCTE membrane is 6 µm thick and contains track-etched cylindrical pores with a diameter of 10 nm and pore density of $6 \times 10^8/cm^2$ (FIG. 2.2a). The AAO membrane is 60 µm thick and contains 20 nm cylindrical pores at the face of the membrane in contact with the feed solution. These pores run parallel to one another for approximately 2 µm and then feed much larger (200 nm in diameter) pores that run parallel to one another through the remaining thickness of the membrane. The pore density of the AAO membrane at the entrance (i.e., in contact with the feed solution) is around $6 \times 10^{14}/cm^2$ (FIGS. 2.2b,c).[21]

The feed solution contained 25 mg of chitosan in 20 mL of 10-3 M HCl (pH=3.0). The receiver solution was 10 mL of $10^{-3}$ M NaOH (pH=11). The area of membrane exposed to these solutions, either PCTE or AAO, was 2 $cm^2$. Gravity flow was achieved via a height difference between the two solutions, causing the low pH chitosan feed solution to flow into the high pH receiver solution. Nanodroplets are formed at the outlet of the PCTE nanoporous membrane in contact with the high pH solution, causing precipitation of the chitosan. In the case of the AAO membrane, the precipitation occurs at the exits of the 20 nm nanopores, which feed the 200 nm nanopores in this structure. The chitosan nanoparticles (CSNPs) are carried away from the membrane by the constant gravity flow. No instances of clogging or sticking were found. Nanoparticles were collected from the receiver solution by filtration, rinsed three times with deionized water, and dried in air at room temperature. We obtained 4.2 µg of nanoparticles per hour by PCTE, and 610 µg of nanoparticles per hour by AAO. These differing values are caused by the large pore density difference between the two kinds of nanoporous membranes. By replacing the gravity flow with pressure flow, we achieved in the AAO membrane the production rate of 36 mg/h but with an increase of the diameter of the nanoparticle to about 45 nm.

CSNPs were imaged using a TEM-1230 (JEOL) electron microscope, operated at 100 kV. Samples were deposited on carbon-coated copper grids and negatively stained with 1% uranyl acetate. FIG. 2.3a shows a typical TEM image of the CSNP obtained using the PCTE membrane having 10 nm nanopores. The nanoparticles were found to have a mean diameter of 5 nm. FIG. 2.3b shows that CSNPs obtained using the AAO membrane. These nanoparticles have a mean diameter of 21 nm, which suggests that they are formed at the exit of the smaller nanopores (20 nm) in the AAO membrane.

Dynamic light scattering (DLS), measured with a Zetasizer Nano ZS (Malvern Instruments, Malvern, Pa.), was used to obtain hydrodynamic particle diameters. The hydrodynamic diameters of the particles obtained using the PCTE and AAO membranes were 8 and 26 nm, respectively (FIG. 2.4). The particle size from DLS is slightly larger than the diameter estimated using electron microscopy because DLS measures the diameter of the particles while still in solution, whereas TEM provides the diameter of the particles after thorough drying.[22] That larger particles are obtained using the AAO membrane reflects the fact that the pore diameter in contact with the receiver solution is 20 nm for this membrane versus 10 nm for the PCTE membrane.

We also investigated the effect of flow rate of chitosan solution on the particle-formation process. CSNPs obtained using the AAO membrane were used in these studies. The flow rate of chitosan solution was varied from 7.2 to 32 µL $min^{-1}$ $cm^{-2}$ by adjusting the height difference between the feed and receiver solutions. DLS measurements were used to obtain the particle diameters. Particle diameter was found to increase exponentially with flow rate, over the flow-rate range investigated (FIG. 2.5). At higher flow rates hollow nanotubes and solid nanowires are formed as found from SEM images (not shown). It was also found that the narrowest particle size distribution was obtained at a flow rate of 7.2 µL $min^{-1}$ $cm^{-2}$.

The viscosity of the chitosan feed solution also has a profound effect on nanoparticle-formation process. The viscosity of chitosan feed solution was varied by adding glycerol, while maintaining its pH at 3. Particle sizes initially increased with viscosity but leveled at higher viscosities (FIG. 2.6). We suggest that this is caused by a change in the diffusion rate, which decreases rapidly as the viscosity increases, causing larger particles to be formed at slower diffusion rates. When the viscosity of chitosan solution achieves a certain point, particle size stops growing, perhaps owing to the gravity-induced detachment of the nanodroplets from the smaller nanopores in the membrane into the sodium hydroxide solution. The ultimate size is limited by the larger, 200 nm nanopores in the AAO structure.

For the drug loading and encapsulation study, we use rhodamine 6G (R6G) as a model system to mimic a drug molecule. The organic molecule R6G is one of the most often used fluorescent dyes with excitation and emission wavelengths at 525 and 555 nm, respectively.[23,24] Using such a fluorescent model compound provides us with a rapid method to evaluate the encapsulation data, which in turn allows us to optimize the process parameters.

In our experiment, 5.0 wt % R6G is premixed with the chitosan solution. FIG. 2.7 shows the TEM images of R6Gloaded chitosan nanoparticles obtained using the PCTE and AAO membranes, respectively, and FIG. 2.8 shows the corresponding results obtained using dynamic light scattering.

The amount of R6G encapsulated in the chitosan particle was determined by dissolving the dry particles in a phosphate/citrate buffer solution at pH=3 followed by fluorescence measurements of the released R6G. When 5.0 wt % of R6G, referred to the weight of chitosan, was added to the feed solution and the PCTE membrane was used, the amount of R6G incorporated into the nanoparticles was 2.7 wt % (Table 1). The amount incorporated into the particles prepared using the AAO membrane was 3.3 wt %. Table 1 summarized these results and includes the polydispersity index (PDI) values.

TABLE 1

Statistical Size and Encapsulation Efficiency Data for Chitosan (CS) and Chitosan-Rhodamine 6G (CS-R6G) Nanoparticles

| membrane | nanoparticle | diameter TEM (nm) | diameter DIS (nm) | PDI | encapsulation ratio (%) |
|---|---|---|---|---|---|
| PCTE | CS | 5 ± 2 | 8 ± 1 | 0.204 | |
| PCTE | CS-R6G | 5 ± 3 | 9 ± 2 | 0.108 | 2.7 |
| AAO | CS | 21 ± 5 | 26 ± 2 | 0.228 | |
| AAO | CS-R6G | 30 ± 8 | 30 ± 4 | 0.333 | 3.3 |

Conclusion:

The method of flowing liquid through a nanoporous membrane provides a general technique for incorporating guest molecules in the host chitosan nanoparticles. We believe that many other biodegradable polymer systems can be loaded with different organic compounds, which suggests the practical use of this technique in preparing pharmaceuticals in nanoparticle form for drug delivery.

References for Example 2, each of which is incorporated herein by reference:

(1) Kost, J.; Langer, R. *Adv. Drug Delivery Rev.* 2001, 46, 125.
(2) Farokhzad, O.; Langer, R. *ACS Nano.* 2009, 3, 16-20.
(3) Nell, a. E.; Ma dler, L.; Velegol, D.; Xia, T.; Hoek, E. M. V.; Somasundaran, P.; Klaessig, F.; Castranova, V.; Thompson, M. *Nat. Mater.* 2009, 8, 543-557.
(4) Jacobson, G. B.; Shinde, R.; Contag, C. H.; Zare, R. N. *Angew. Chem., Int. Ed.* 2008, 47, 7880-7882.
(5) Jacobson, G. B.; Gonzalez-Gonzalez, E.; Spitler, R.; Shinde, R.; Leake, D.; Kaspar, R. L.; Contag, C. H.; Zare, R. N. *J. Pharm. Sci.*, in press.
(6) Jacobson, G. B.; Shinde, R.; McCullough, R. L.; Chen, N. J.; Creasman, A.; Beyene, A.; Quan, C.; Hickerson, R. P.; Turner, C.; Kaspar, R. L.; Contag, C. H.; Zare, R. N. *J. Pharm. Sci.* [Online early edition]. DOI: 10.1002/jps.22035.
(7) Buyukserin, F.; Medley, C. D.; Mota, M. O.; Kececi, K.; Rogers, R. R.; Tan, W.; Martin, C. R. *Nanomedicine (London)* 2008, 3, 283-292.
(8) Hillebrenner, H.; Buyukserin, F.; Stewart, J. D.; Martin, C. R. *Nanomedicine (London)* 2006, 1, 39-50.
(9) Allan, G. G.; Fox, J. G.; Crosby, G. D.; Sarkanen, K. V. *Chitosan, a mediator for fiber-water interactions in paper. College of Forest Resources*; University of Washington Press, Seattle, Wash., 1977; p 125.
(10) Agnihotri, S.; Mallikarjuna, N.; Aminabhavi, T. *J. Controlled Release* 2004, 100, 5-28.
(11) Senel, S.; McClure, S. *J. Adv. Drug Delivery Rev.* 2004, 56, 1467-1480.
(12) Berger, J.; Reist, M.; Mayer, J. M.; Felt, O.; Peppas, N. A.; Gurny, R. *Eur. J. Pharm. Biopharm.* 2004, 57, 19-34.
(13) Yi, H.; Wu, L.; Bentley, W. E.; Ghodssi, R.; Rubloff, G. W.; Culver, J. N.; Payne, G. F. *Biomacromolecules* 2005, 6 (6), 2881-2894.
(14) Vfirum, K.; Ottoy, M.; Smidsrod, O. *Carbohydr. Polym.* 1994, 25, 65-79.
(15) Anna, S. L.; Bontoux, N.; Stone, H. A. *Appl. Phys. Lett.* 2003, 82, 364-366.
(16) Xu, S.; Nie, Z.; Seo, M.; Lewis, P.; Kumacheva, E.; Stone, H. A.; Garstecki, P.; Weibel, D. B.; Gitlin, I.; Whitesides, G. W. *Angew. Chem., Int. Ed.* 2005, 44, 724-728.
(17) Powell, M. R.; Sullivan, M.; Vlassiouk, I.; Constantin, D.; Sudre, O.; Martens, C. C.; Eisenberg, R. S.; Siwy, Z. S. *Nat. Nanotechnol.* 2008, 3, 51-57.
(18) Hulteen, J.; Martin, C. R. *J. Mater. Chem.* 1997, 7, 1075-1087.
(19) Mitchell, D. T.; Lee, S. B.; Trofin, L.; Li, N.; Nevanen, T. K.; Soederlund, H.; Martin, C. R. *J. Am. Chem. Soc.* 2002, 124, 11864-11865.
(20) Gasparac, R.; Kohli, P.; Paulino, M. O. M.; Trofin, L.; Martin, C. R. *Nano Lett.* 2004, 4, 513-516.
(21) Srivastava, D.; Lee, I. *Adv. Mater.* 2006, 18, 2471-2475.
(22) Cumberland, S. A.; Lead, J. R. *J. Chromatogr., A* 2009, 1216, 9099-9105.
(23) Avnir, D.; Levy, D.; Reisfeld, R. *J. Phys. Chem.* 1984, 88, 5956-5959.
(24) Eniolaa, A. O.; Rodgersa, S. D.; Hammer, D. A. *Biomaterials* 2002, 23, 2167-2177.

Example 3

Brief Introduction

We report a straightforward, bottom-up, scalable process for preparing mineralized nanofibers. Our procedure is based on flowing feed solution, containing both inorganic cations and polymeric molecules, through a nanoporous membrane into a receiver solution with anions, which leads to the formation of mineralized nanofibers at the exit of the pores. With this strategy, we were able to achieve size control of the nanofiber diameters. We illustrate this approach by producing collagen fibrils with calcium phosphate incorporated inside the fibrils. This structure, which resembles the basic constituent of bones, assembles itself without the addition of noncollagenous proteins or their polymeric substitutes. Rheological experiments demonstrated that the stiffness of gels derived from these fibrils is enhanced by mineralization. Growth experiments of human adipose derived stem cells on these gels showed the compatibility of the fibrils in a tissue-regeneration context.

Discussion:

Nanofibers can be generated in numerous ways, such as electrospinning and self-assembly and with different materials like natural and artificial polymers or amphiphilic peptides.[1-6] Mineralization of nanofibers has been pursued with a major goal being the preparation of a material that resembles the basic structure of mammalian bone.[4,7-12] In this Example, we present a new and straightforward method for the preparation of mineralized collagen fibrils that closely resemble natural bone material. Our strategy was based on a nanoporous polycarbonate track etched (PCTE) membrane that separated two liquids, a feed solution and a receiver solution. This approach was used previously to prepare nanoparticles[13] but we extend it here to produce fibrils. Fibrils were formed by pumping the feed solution through the membrane into the receiver solution. The feed solution contained calcium cations (Ca2þ) and monomolecular tropocollagen. The receiver solution contained phosphate anions ($HPO_4^{2-}$), which induced precipitation of the inorganic salt along and within the collagen fibrils. This method has the appeal that it is readily scalable.

Organisms produce a wide variety of organic-inorganic hybrid materials called biominerals. The most common biominerals are the phosphate and carbonate salts of calcium that are found in conjunction with organic polymers, such as collagen and chitin, to give structural support to bones and shells. Biomineralization has inspired chemists to seek new synthetic strategies for creating inorganic materials in complex forms, for example, by pattern recognition of self-organized organic assemblies.[14,15] Along with the advancement of our understanding of biological processes, the main goal of these studies is to find new materials for bone grafting, tissue engineering, or other medical applications.

The nature of the interaction between organic matrix and inorganic mineral in biomineralization processes has long been a subject of debate. Early evidence led to the view that crystal growth was guided by epitaxy with the organic matrix as a template. Later, several nonclassical crystallization pathways have been proposed for biomineralization. In the last several years, evidence for the importance of an amorphous precursor phase has rapidly accumulated and now is the dominant view in the field. It has been found that acidic noncollagenous proteins play an important role in facilitating the amorphous phase.[32] Acidic hydrophilic polymers have been used to mimic these noncollagenous proteins. As has been established by several studies, the role of the acidic polymer is two-fold: it suppresses bulk crystallization of the mineral and stabilizes the amorphous phase. With this approach, preassembled collagen fibrils could be mineralized with calcium phosphate. This could be achieved with the use of polyanionic polymers like polyaspartate or polylactate.[7-9] As will be seen in what follows, our method removes the need of using polyanionic polymers in preparing fibrils.

Triple-helical single tropocollagen molecules spontaneously self-assemble into fibrils under the right conditions.[35, 10,36-40] In collagen fibrils, each triple helix is shifted relative to its molecular neighbor by 40 nm in the direction of the helix and overlaps the adjacent molecule by 27 nm, which results in the characteristic 67 nm spaced band pattern of collagen fibrils (FIG. 3.1). Laterally, the helices are arranged in a hexagonal pattern with respect to each other within the fibril. Collagen fibrils are most stable at moderately basic pH (9-11) and high ion (especially phosphate) concentrations.

Using the method presented in this paper, it was possible to incorporate calcium phosphate (CaP) into collagen fibrils without any additional polymers or proteins. We achieved the simultaneous formation of collagen fibrils and amorphous CaP at the exit of the pores in the PCTE membrane. Therefore, we found a new bottom-up approach for the artificial formation of the basic building blocks of bone. We use the abbreviation CaP to denote calcium phosphate, although it is not presently known the exact chemical composition and morphology of this phosphate salt of calcium.

The rheology of gels derived from highly concentrated fibril suspensions was investigated to understand the mechanical properties of the fibrils. To demonstrate the biomedical usefulness of the fibrils generated with this approach in a tissue-engineering context, human adipose derived stem cells (hADSCs) were grown on substrates made of collagen fibril aggregates.

Materials:

All chemicals were purchased from Sigma Aldrich (St. Louis, Mo.) and used without further purification. Calcium chloride ($CaCl_2$) and dibasic sodium monohydrogen phosphate (Na2HPO4) were prepared fresh daily using Millipore water. Type I tropocollagen from rat tails was purchased from BD Biosciences (Bredford, Mass.). Stock solutions were 3 mg/mL tropocollagen in 0.1 M acetic acid. PBS buffer (10×) was obtained from Invitrogen (Carlsbad, Calif.).

U-Tube Setup:

The U-tube setup consisted of two half U-tubes and a nanoporous membrane sandwiched between the two halves (FIG. 4.1). Polycarbonate track-etched (PCTE) nanoporous membranes (Whatman, Nuclepore Track-Etch Membrane, Florham Park, N.J.) with pore diameters between 50 nm and 1 μm were used in our experiments. For the preparation of collagen fibrils, one-half of the U-tube was filled with 6 mL of feed solution containing 1 mg/mL collagen, 1-20 mM $CaCl_2$, and 1 mM HCl (pH 3.0); the other half was filled with 4 mL of receiver solution containing 0.66 mM $Na_2HPO_4$ and 1 mM NaOH. A gauge pressure of 250 mbar was created by connecting a compressed air outlet with a pressure reduction valve to the feed solution side of the U-tube. In this way, the feed solution was pumped into the receiver solution according to the applied pressure. Fibrils were collected by filtration through PCTE membranes and dried at room temperature. The PCTE membranes that were used for filtration (not to be confused with the ones used for fibril formation) also served as the substrate for scanning electron microscopy (SEM). To investigate the influence of filtration on artifact formation, different kinds of membranes with different pore sizes were used for the last filtration step in control experiments. Regardless of the type of filter used, the fibrils always had the same appearance.

SEM:

Scanning electron microscopy images were acquired using an FEI XL30 Sirion SEM. Dry samples on carbon sticky tape were sputter-coated for 120 s at 15 mA with Pd/Au. The diameters of the fibrils were evaluated with the software ImageJ.

TEM:

Transmission electron microscopy (TEM) was carried out using a FEI Tecnai G2 F20 X-TWIN. Samples were deposited on Formvar carbon-coated copper grids without prior filtration. Coupled to the TEM was selected area electron diffraction (SAED) and energy disperse X-ray spectroscopy (EDS).

Preparation of Gels for Rheology:

To prepare gels from the fibril suspensions (obtained as described above, using a pore size of 200 nm), the suspensions were dialyzed for 24 h using a seamless cellulose membrane (width=32 mm; diameter=20.4 mm; pore size=4 nm; Fisher Science Education, Rochester, N.Y.). Poly(ethylene glycol) was the drying agent. The samples were afterward filtrated through a 50 nm PCTE membrane until they were completely dried. The samples derived from collagen fibrils were swelled for 1 h in 10×PBS buffer directly before the measurements.

Rheological Measurements:

The rheological experiments were carried out using a TA AR-G2 equipped with an 8 mm parallel plate geometry. While the plate geometry was oscillated at a frequency ω, we measured the torque (stress) that was required to arrive at a certain deformation (strain). The frequency sweep tests were carried out with a strain of γ=0.1%.

Preparation of Substrates for Stem Cell Experiments:

The fibril scaffolds used for stem cell culture were prepared by filtering fibril suspensions (obtained as described above, using a pore size of 200 nm) on a 50 nmPCTE nanoporous membrane until the filter surface was completely covered (confirmed by SEM). Three types of fibril samples were prepared into scaffolds: collagen, collagen/CaP (1 mM $CaCl_2$), collagen/CaP (5 mM $CaCl_2$). Resulting scaffolds were rinsed with deionized water for three times and dried at room temperature.

Stem Cell Experiments:

Human adipose-derived stem cells (hADSCs) were isolated from donors and expanded in culture. Cells were cultured in Dulbecco Modified Eagle Medium (DMEM) supplemented with 10% fetal bovine serum, 1% penicillin/streptomycin, and 0.05% fibroblast growth factor. Two-dimensional sheets of fibrils prepared on PCTE filter membranes were placed at the base of a 96 well plate (n=3). Trypsin was added to the hADSCs to remove them from cell culture flasks and 8×10³ cells were seeded per well in 200 μL of media further supplemented with β-glycerolphosphate, ascorbic-2-phosphate, dexamethasone, and sodium pyrinate. Cells were cultured for 16 days and media was refreshed every second day.

Cell Titer:

CellTiter 96 (Promega Corp.) assay was performed to quantify cell proliferation at days 5, 11, and 16. Cell media was removed and CellTiter 96 AQueous One Solution was added to the cells. Quantification was performed with a microplate reader according to the manufacturer's protocol.

Cell Imaging:

Following cell culture, cells were fixed with 4% paraformaldehyde for 15 min and washed extensively with phosphate buffered saline solution (PBS). Fluorescein isothiocyanate (FITC) phalloidin (Santa Cruz Biotechnology) was used to stain the actin filaments and samples were mounted with VECTASHIELD HardSet Mounting Media containing 40,6-diamidino-2-phenylindole (DAPI).

Statistics:

Statistics was performed using MiniTab. A Tukeys comparison determined differences between time points and groups ($p<0.05$ was considered as statistically different). Data were presented as mean=1 standard deviation.

Results and Discussion:

Using the U-tube setup (FIG. 3.1), a feed solution containing 1 mg/mL tropocollagen in an acidic medium (diluted HCl) was pumped through a nanoporous PCTE membrane into a receiver solution containing sodium hydroxide at pH 11. Using these parameters, discrete collagen fibrils with a uniform diameter were obtained (FIG. 3.2A, B). The diameter of the fibrils could be controlled by choosing the pore diameter of the PCTE membranes while maintaining all other parameters. Collagen fibrils formed using pore diameters of 1 μm, 400 nm, and 200 nm exhibited diameters of 760±240, 270±120, and 120±30 nm, respectively. Collagen fibril formation blocked pores smaller than 200 nm. Uncontrolled fibril formation, as was shown by adding 1 mL feed solution to 3 mL receiver solution without membrane, resulted in the precipitation of unstructured collagen aggregates that remained as a dense film on the substrate. The length of the fibril is variable but often exceeds tens of micrometers.

To obtain mineralized collagen fibrils, calcium chloride ($CaCl_2$) was added to the feed solution and sodium monohydrogen phosphate ($Na_2HPO_4$) was added to the receiver solution. A 200 nm PCTE membrane was used throughout these experiments. The formation of mineralized fibrils was particularly sensitive to the calcium concentration. With lower calcium concentrations (1 mM $CaCl_2$ in the feed solution), only the interior of the fibrils was mineralized, as clearly seen by the visible enhancement of the band pattern of the collagen fibrils (compare FIG. 3.2 panel B to panel D; without staining, the band pattern is not visible in unmineralized fibrils with TEM). With higher calcium concentrations (2.5 mM and 5 mM $CaCl_2$), the fibrils exhibited a mineralized overgrowth (FIG. 3.2E, F, G, H). A closer examination of the overgrowth revealed segments with spacing on the order of 67 nm, which equals the distance found in the band pattern of collagen fibrils. With $CaCl_2$ concentrations as high as 20 mM, platelike hydroxyapatite crystals precipitated in large bundles that were interconnected by collagen (data not shown).

The existence of calcium phosphate in the fibrils was determined by EDS that was coupled to the TEM. Calcium phosphate was observed in the collagen/CaP (1 mM $CaCl_2$) and collagen/CaP (5 mM $CaCl_2$) samples. EDS also revealed that the amounts of calcium phosphate within the fibrils increased with the $CaCl_2$ concentration in the feed solution. The EDS of a pure collagen fibrils served as a control sample in which the characteristic peaks of calcium and phosphate were not observed. SAED showed that the mineral phase was always amorphous (see insets in FIG. 3.2).

The prevalence of the amorphous phase was a result of the rapid flow of the feed solution that created a highly supersaturated phase at the exit of the pores. Heterogeneous nucleation of amorphous calcium phosphate was guided by the gaps between the collagen molecules. The gaps also provided room for growth in an otherwise spatially constrained environment. A rough estimation of the flow rate of the feed solution through a PCTE membrane with a pore size of 200 nm gave a pore velocity of approximately 100 μm/s. This yielded a characteristic extensional flow gradient into such a pore of 1000/s. This rate can be compared to the rotational diffusivity of collagen, which is approximately 810/s.[43] These two rates can be combined to provide an estimate of the Deborah number, De=1.2. This dimensionless group, which gauges the propensity of a flow to orient the chains, was somewhat greater than unity, suggesting that the collagen adopted a preferential orientation parallel to the pore axis. In contrast, reaction times of at least four days for the formation of a crystalline phase of calcium phosphate were found in the literature.[7] This fast and coincident formation of fibrils and CaP produced a collagen/CaP composite material without the addition of acidic polymers or natural noncollagenous proteins that are typically involved in bone growth.

To compare the viscoelastic properties of gels produced from the different kinds of fibrils, the shear rheology of gels prepared from highly concentrated fibril suspensions was investigated. With rheological experiments, it is possible to obtain the dynamic elastic modulus, G0, and the dynamical viscous modulus, G00. The rheological experiments revealed that the dynamic moduli strongly increase with increasing calcium phosphate concentration (FIG. 3.3). Compared to pure collagen fibrils, the collagen/CaP fibrils are at least an order of magnitude stiffer. It is known that the stiffness of a gel influences cell differentiation.[44]

The fibrils were tested for their ability to support cell growth in vitro using human adipose-derived stem cells (hADSCs) as a model cell line for tissue engineering. This cell type is found in abundance within the human body and is capable of differentiating down the mesenchymal lineage, making it an excellent candidate for future tissue engineering applications.[45]

Cell growth was quantified using a colorimetric test (CellTiter 96, Promega, Corp.), which permits a count to be made of viable cells. This assay demonstrated increasing proliferation in all groups at all time points with the exception of collagen fibrils at day 16 (FIG. 3.4B). A trend was also found indicating that the inclusion of calcium phosphate enhanced cell proliferation. Interestingly, only the calcium phosphate containing groups exhibited a statistical increase in alkaline phosphatase activity (FIG. 3.4C), which is an early indicator of bone cell differentiation. Xie et al.[46] have shown that calcium phosphate can induce osteoblast differentiation while Sere et al.[47] have shown that by combining calcium phosphate with collagen, cells up regulate matrix production. Our data also show that increased $CaCl_2$ concentration also increased proliferation and alkaline phosphatase production.

Actin staining indicated intimate contact of the cells with the underlying surface, and we also observed out-stretched cells with connecting filopodia. Cells rapidly covered the nanofibrous surface and began to grow in multilayers (FIG. 3.4A).

Conclusions:

We present a new method for preparing mineralized fibrils. This method is able to control the fibril diameter through the choice of the size of the nanopores in a membrane that separates the feed solution from the receiver solution. This work represents to our knowledge the first time that calcium phosphate has been incorporated into collagen fibrils in a onestep process without the use of organic solvents or polyionic additives. This constrained self-assembly process causes the appearance of bands of calcium phosphate inside the fibrils and resembles closely the same structure found in bone. Moreover, this method is simple and can be readily scaled to produce large quantities of nanofibers. In experiments with human adipose derived stem cells, we were able to demonstrate the usefulness of fibers generated with our approach in a tissue-engineering context. One possible application might be bone grafting in which we replace missing bone with the mineralized fibrils, which serve as a scaffold for the regeneration of bone structure. We are encouraged to believe that this scalable process for making mineralized fibrils through nanoporous membranes holds much promise for future studies in tissue engineering and in the production of new types of composite materials.

References for Example 3, each of which is incorporated herein by reference:

(1) Huang, Z.; Zhang, Y.; Kotaki, M.; Ramakrishna, S. Compos. Sci. Technol. 2003, 63, 2223-2253.
(2) Teo, W. E.; Ramakrishna, S. Nanotechnology 2006, 17, R89-R106.
(3) Zhang, S.; Greenfield, M. A.; Mata, A.; Palmer, L. C.; Bitton, R.; Mantei, J. R.; Aparicio, C.; de La Cruz, M. O.; Stupp, S. I. Nat. Mater. 2010, 9 (7), 594-601.
(4) Hartgerink, J. D.; Beniash, E.; Stupp, S. I. Science 2001, 294, 1684.
(5) Zhang, S. Nat. Biotechnol. 2003, 21, 1171-1178.
(6) Kim, B.; Park, H.; Lee, S.; Sigmund, W. M. Mater. Lett. 2005, 59, 829-832.
(7) Olszta, M. J.; Cheng, X.; Jee, S. S.; Kumar, R.; Kim, Y.; Kaufman, M. J.; Douglas, E. P.; Gower, L. B. Mater. Sci. Eng., R 2007, 58, 77-116.
(8) Ehrlich, H.; Hanke, T.; Born, R.; Fischer, C.; Frolov, A.; Langrock, T.; Hoffmann, R.; Schwarzenbolz, U.; Henle, T.; Simon, P. et al. J. Membr. Sci. 2009, 326, 254-259.
(9) Deshpande, A. S.; Beniash, E. Cryst. Growth Des. 2008, 8, 3084-3090.
(10) Zhang, W.; Liao, S. S.; Cui, F. Z. Chem. Mater. 2003, 15, 3221-3226.
(11) Li, X.; Xie, J.; Lipner, J.; Yuan, X.; Thomopoulos, S.; Xia, Y. Nano Lett. 2009, 9, 2763-2768.
(12) Fujihara, K.; Kotaki, M.; Ramakrishna, S. Biomaterials 2005, 26, 4139-4147.
(13) Guo, P.; Martin, C. R.; Zhao, Y.; Ge, J.; Zare, R. N. Nano Lett. 2010, 10, 2202-2206.
(14) Mann, S.; Ozin, G. A. Nature 1996, 382, 313-318.
(15) Estroff, L. A.; Hamilton, A. D. Chem. Mater. 2001, 13, 3227-3235.
(16) Ripamonti, U.; van den Heever, B.; Heliotis, M.; DAL, M.; et al. S. Afr. J. Sci. 2002, 98, 429-433.
(17) Ripamonti, U.; Hari Reddi, A. Crit. Rev. Oral Biol. Med. 1997, 8, 154.
(18) DiMasi, E.; Olszta, M. J.; Patel, V. M.; Gower, L. B. CrystEng-Comm 2003, 5, 346-350.
(19) Heywood, B. R.; Mann, S. Adv. Mater. 1994, 6, 9-20.
(20) Sommerdijk, N. A. J. M.; With, G. D. Chem. Rev. 2008, 108, 4499-4550.
(21) Zhang, L.; Liu, H.; Feng, X.; Zhang, R.; Zhang, L.; Mu, Y.; Hao, J.; Qian, D.; Lou, Y. Langmuir 2004, 20, 2243-2249.
(22) Mann, S.; Archibald, D. D.; Didymus, J. M.; Douglas, T.; Heywood, B. R.; Meldrum, F. C.; Reeves, N. J. Science 1993, 261, 1286.
(23) Mann, S. Nature 1993, 365, 499-505.
(24) Ceolfen, H. Curr. Opin. Colloid Interface Sci. 2003, 8, 23-31.
(25) Tao, J.; Pan, H.; Zeng, Y.; Xu, X.; Tang, R. J. Phys. Chem. B 2007, 111, 13410-13418.
(26) Ceolfen, H. In Biomineralization II; Kensuke, N., Ed.; Springer: New York, 2007; pp 1-77.
(27) Fricke, M.; Volkmer, D. In Biomineralization I; Kensuke, N., Ed.; Springer: New York, 2007; pp 1-41.
(28) Olszta, M. J.; Odom, D. J.; Douglas, E. P.; Gower, L. B. Connect. Tissue Res. 2003, 44, 326-334.
(29) Gower, L. B. Chem. Rev. 2008, 108, 4551-4627.
(30) Weiner, S.; Mahamid, J.; Politi, Y.; Ma, Y.; Addadi, L. Front. Mater. Sci. China 2009, 3, 104-108.
(31) Cheng, X.; Gower, L. B. Biotechnol. Prog. 2006, 22, 141-149.
(32) Marsh, M. E. Protoplasma 1994, 177, 108-122.
(33) Kato, T.; Suzuki, T.; Amamiya, T.; Irie, T.; Komiyama, M.; Yui, H. Supramol. Sci. 1998, 5, 411-415.
(34) Kato, K.; Eika, Y.; Ikada, Y. J. Mater. Sci. 1997, 32, 5533-5543.
(35) Bradt, J.; Mertig, M.; Teresiak, A.; Pompe, W. Chem. Mater. 1999, 11, 2694-2701.
(36) Gobeaux, F.; Mosser, G.; Anglo, A.; Panine, P.; Davidson, P.; Giraud-Guille, M.; Belamie, E. J. Mol. Biol. 2008, 376, 1509-1522.
(37) Orgel, J. P. R. O.; Irving, T. C.; Miller, A.; Wess, T. J. Proc. Nat. Acad. Sci. U.S.A. 2006, 103, 9001-9005.
(38) Eglin, D.; Mosser, G.; Giraud-Guille, M.; Livage, J.; Coradin, T. Soft Matter 2005, 1, 129.
(39) Kadler, K. E.; Holmes, D. F.; Trotter, J. A.; Chapman, J. A. Biochem. J. 1996, 316, 1-11.
(40) Weis, K.; Pompe, W.; Bradt, J. Process for the preparation of mineralized collagen fibrils and their use as bone substitute material.
(41) Bruns, R. R.; Gross, J. Biopolymers 1974, 13, 931-941.
(42) Chapman, J. A. Connect. Tissue Res. 1974, 2, 137-150.
(43) Fletcher, G. C. Biopolymers 1976, 15, 2201-2217.
(44) Engler, A. J.; Sen, S.; Sweeney, H. L.; Discher, D. E. Cell 2006, 126, 677-689.
(45) Strem, B. M.; Hicok, K. C.; Zhu, M.; Wulur, I.; Alfonso, Z.; Schreiber, R. E.; Fraser, J. K.; Hedrick, M. H. The Keio journal of medicine 2005, 54, 132-141.
(46) Xie, J.; Baumann, M. J.; McCabe, L. R. J. Biomed. Mater. Res. 2004, 71A, 108-117.
(47) Serre, C.; Papillard, M.; Chavassieux, P.; Boivin, G. Biomaterials 1993, 14, 97-106.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of making chitosan nanostructures, comprising:
providing a structure having a first compartment for a feed solution and a second compartment for a receiver solution, wherein the feed solution comprises chitosan, and wherein a polycarbonate or an alumina nanoporous membrane structure having nanochannels is positioned between an end of the first compartment and an end of the second compartment;
causing the feed solution to flow through the nanoporous membrane structure from the end of the first compartment to the end of the second compartment;
forming nanostructures comprising the chitosan at the opening of the nanochannels; and
collecting the chitosan nanostructures from the receiver solution.

2. The method of claim 1, wherein causing the feed solution to flow through the nanoporous membrane structure having nanochannels from the first compartment to the second compartment is conducted as a continuous flow.

3. The method of claim 1, wherein causing the feed solution to flow is the result of a flow selected from the group consisting of: an osmotic flow, a pressure flow, gravity flow, and a combination thereof.

4. The method of claim 1, wherein forming nanostructures is the result of a change in a condition, wherein the condition is selected from the group consisting of: solvent, pH, temperature, salt content, chemical concentration, and a combination thereof.

5. The method of claim 1, wherein the chitosan nanostructure is selected from the group consisting of: a nanoparticle, a nanowire, or a nanosheet.

6. The method of claim 1, wherein the nanochannels have a diameter of about 1 nm to 1 pm.

7. The method of claim 1, wherein the nanochannels have a length of about 1 nm to 500 pm.

8. The method of claim 1, wherein the chitosan nanostructure is configured to pass through a circular opening having diameter of about 1 nm to 1 pm.

9. The method of claim 8, wherein the chitosan nanostructure has a length in any direction of about 1 nm to 1 m.

10. The method of claim 1, wherein the chitosan nanostructure has a width in any direction of about 1 nm to 1 pm, a height in any direction of about 1 nm to 1 pm, and a length in any direction of about 1 nm to 100 pm.

11. The method of claim 1, wherein the chitosan nanostructure includes two different types of materials.

12. The method of claim 11, wherein one of the types of materials is a pharmaceutical agent and the other of the materials is a biodegradable agent.

13. The method of claim 1, wherein the feed solution includes a material selected from the group consisting of: ions, an organic molecule, a lipid, a pharmaceutical agent, a protein, a gene material, a molecular imaging probe, and a combination thereof.

14. The method of claim 1, wherein causing the feed solution to flow is the result of an osmotic flow.

* * * * *

UNITED STATES PATENT AND TRADEMARK OFFICE
CERTIFICATE OF CORRECTION

PATENT NO.         : 9,801,829 B2
APPLICATION NO.    : 13/457609
DATED              : October 31, 2017
INVENTOR(S)        : Guo et al.

It is certified that error appears in the above-identified patent and that said Letters Patent is hereby corrected as shown below:

In the Claims

At Column 20, Line 13, in Claim 6, delete:
"a diameter of about 1 urn to 1 pm.,"
And replace with:
--a diameter of about 1 urn to 1 μm.,--

AND
At Column 20, Line 16, in Claim 7, delete:
"a length of about 1 nm to 500 pm.,"
And replace with:
--a length of about 1 nm to 500 μm.--

AND
At Column 20, Line 18, in Claim 8, delete:
"having diameter of about 1 nm to 1 pm.,"
And replace with:
--having a diameter of about 1 nm to 1 μm.--

AND
At Column 20, Line 24, in Claim 10, delete:
"in any direction of about 1 nm to 100 pm."
And replace with:
--in any direction of about 1 nm to 100 μm.--

Signed and Sealed this
Thirtieth Day of January, 2018

Joseph Matal
*Performing the Functions and Duties of the
Under Secretary of Commerce for Intellectual Property and
Director of the United States Patent and Trademark Office*